US008202875B2

(12) United States Patent
Fischer et al.

(10) Patent No.: US 8,202,875 B2
(45) Date of Patent: Jun. 19, 2012

(54) SELECTIVE INSECTICIDES BASED ON SUBSTITUTED CYCLIC KETOENOLS AND SAFENERS

(75) Inventors: Reiner Fischer, Monheim (DE); Udo Reckmann, Köln (DE); Christopher Hugh Rosinger, Hofheim am Taunus (DE); Erich Sanwald, Kiel (DE); Christian Arnold, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 983 days.

(21) Appl. No.: 11/572,400

(22) PCT Filed: Jul. 18, 2005

(86) PCT No.: PCT/EP2005/007794
§ 371 (c)(1),
(2), (4) Date: Jul. 22, 2008

(87) PCT Pub. No.: WO2006/008111
PCT Pub. Date: Jan. 26, 2006

(65) Prior Publication Data
US 2009/0012100 A1    Jan. 8, 2009

(30) Foreign Application Priority Data

Jul. 20, 2004  (DE) .................. 10 2004 035 133

(51) Int. Cl.
*A01N 43/08* (2006.01)
*A01N 43/10* (2006.01)
*A01N 43/16* (2006.01)
*A01N 43/36* (2006.01)
*A01N 35/06* (2006.01)

(52) U.S. Cl. ........ 514/256; 514/409; 514/616; 514/378; 514/403; 514/311; 514/628; 514/374

(58) Field of Classification Search .......... None
See application file for complete search history.

(56) References Cited

U.S. PATENT DOCUMENTS

| | | |
|---|---|---|
| 4,021,224 A | 5/1977 | Pallos et al. |
| 4,091,006 A | 5/1978 | Durden, Jr. et al. |
| 4,175,135 A | 11/1979 | Haines |
| 4,186,130 A | 1/1980 | Teach |
| 4,209,432 A | 6/1980 | Roth |
| 4,209,532 A | 6/1980 | Wheeler |
| 4,256,657 A | 3/1981 | Wheeler |
| 4,256,658 A | 3/1981 | Wheeler |
| 4,256,659 A | 3/1981 | Wheeler |
| 4,257,858 A | 3/1981 | Wheeler |
| 4,283,348 A | 8/1981 | Wheeler |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,436,666 A | 3/1984 | Wheeler |
| 4,526,723 A | 7/1985 | Wheeler et al. |
| 4,551,547 A | 11/1985 | Wheeler |
| 4,613,617 A | 9/1986 | Sousa |
| 4,623,727 A | 11/1986 | Hübele |
| 4,632,698 A | 12/1986 | Wheeler |
| 4,639,266 A | 1/1987 | Heubach et al. |
| 4,659,372 A | 4/1987 | Wheeler |
| 4,881,966 A | 11/1989 | Nyffeler et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,094,681 A | 3/1992 | Krämer et al. |
| 5,116,836 A | 5/1992 | Fischer et al. |
| 5,258,527 A | 11/1993 | Krauskopf et al. |
| 5,262,383 A | 11/1993 | Fischer et al. |
| 5,314,863 A | 5/1994 | Löher et al. |
| 5,332,720 A | 7/1994 | Krüger et al. |

(Continued)

FOREIGN PATENT DOCUMENTS

AU    34951/89 A    11/1989

(Continued)

OTHER PUBLICATIONS

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

(Continued)

*Primary Examiner* — Johann Richter
*Assistant Examiner* — Erin Hirt
(74) *Attorney, Agent, or Firm* — Sterne, Kessler, Goldstein & Fox PLLC

(57) ABSTRACT

The present invention relates to the use of selective insecticidal compositions, characterized in that they comprise an effective amount of an active compound combination comprising (a) at least one compound of the formula (I)

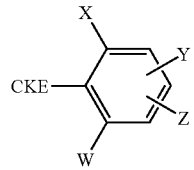

(I)

in which CKE, W, X, Y and Z are as defined in the description, and (b) at least one crop plant compatibility-improving compound, from the group of compounds mentioned in the description, for controlling insects and/or arachnids, and to a method for controlling insects and/or arachnids using the compositions.

29 Claims, No Drawings

U.S. PATENT DOCUMENTS

| | | | |
|---|---|---|---|
| 5,380,852 A | 1/1995 | Schütze et al. | |
| 5,393,729 A | 2/1995 | Fischer et al. | |
| 5,401,700 A | 3/1995 | Sohn et al. | |
| 5,407,897 A | 4/1995 | Cary et al. | |
| 5,494,890 A | 2/1996 | Cederbaum et al. | |
| 5,504,057 A | 4/1996 | Fischer et al. | |
| 5,516,750 A | 5/1996 | Willms et al. | |
| 5,565,450 A | 10/1996 | Fischer et al. | |
| 5,567,671 A | 10/1996 | Fischer et al. | |
| 5,589,469 A | 12/1996 | Fischer et al. | |
| 5,610,122 A | 3/1997 | Fischer et al. | |
| 5,622,917 A | 4/1997 | Fischer et al. | |
| 5,677,449 A | 10/1997 | Fischer et al. | |
| 5,683,965 A | 11/1997 | Bachmann et al. | |
| 5,700,758 A | 12/1997 | Rösch et al. | |
| 5,739,079 A | 4/1998 | Holdgrün et al. | |
| 5,808,135 A | 9/1998 | Fischer et al. | |
| 5,811,374 A | 9/1998 | Bertram et al. | |
| 5,830,825 A | 11/1998 | Fischer et al. | |
| 5,830,826 A | 11/1998 | Fischer et al. | |
| 5,840,661 A | 11/1998 | Fischer et al. | |
| 5,945,444 A | 8/1999 | Fischer et al. | |
| 5,977,029 A | 11/1999 | Fischer et al. | |
| 6,071,937 A | 6/2000 | Bretschneider et al. | |
| 6,114,374 A * | 9/2000 | Lieb et al. | 514/424 |
| 6,133,296 A | 10/2000 | Lieb et al. | |
| 6,200,932 B1 | 3/2001 | Fischer et al. | |
| 6,235,680 B1 | 5/2001 | Ziemer et al. | |
| 6,251,827 B1 | 6/2001 | Ziemer et al. | |
| 6,251,833 B1 | 6/2001 | Erdelen et al. | |
| 6,358,887 B1 | 3/2002 | Fischer et al. | |
| 6,410,480 B1 | 6/2002 | Mühlebach et al. | |
| 6,515,184 B1 | 2/2003 | Fischer et al. | |
| 6,555,499 B1 | 4/2003 | Glock et al. | |
| 6,589,976 B1 | 7/2003 | Fischer et al. | |
| 6,642,180 B1 * | 11/2003 | Fischer et al. | 504/246 |
| 6,806,264 B2 * | 10/2004 | Lieb et al. | 514/183 |
| 6,861,391 B1 | 3/2005 | Fischer et al. | |
| 6,906,007 B2 * | 6/2005 | Fischer et al. | 504/292 |
| 6,994,866 B2 | 2/2006 | Fischer et al. | |
| 7,060,692 B2 | 6/2006 | Fischer et al. | |
| 7,084,138 B2 | 8/2006 | Fischer et al. | |
| 7,432,225 B2 * | 10/2008 | Fischer et al. | 504/105 |
| 7,585,887 B2 | 9/2009 | Fischer et al. | |
| 7,718,706 B2 * | 5/2010 | Lieb et al. | 514/681 |
| 7,727,933 B2 * | 6/2010 | Fischer et al. | 504/283 |
| 7,888,285 B2 | 2/2011 | Fischer et al. | |
| 2001/0004629 A1 | 6/2001 | Lieb et al. | |
| 2002/0010204 A1 | 1/2002 | Lieb et al. | |
| 2002/0022575 A1 | 2/2002 | Fischer et al. | |
| 2002/0072617 A1 | 6/2002 | Hagemann et al. | |
| 2002/0188136 A1 | 12/2002 | Lieb et al. | |
| 2003/0045432 A1 | 3/2003 | Fischer et al. | |
| 2003/0073851 A1 | 4/2003 | Lieb et al. | |
| 2003/0096806 A1 | 5/2003 | Lieb et al. | |
| 2003/0171219 A1 | 9/2003 | Lieb et al. | |
| 2003/0171220 A1 | 9/2003 | Ziemer et al. | |
| 2003/0199572 A1 | 10/2003 | Lieb et al. | |
| 2003/0212086 A1 | 11/2003 | Fischer et al. | |
| 2003/0216260 A1 | 11/2003 | Ruther et al. | |
| 2003/0228984 A1 | 12/2003 | Hagemann et al. | |
| 2004/0019061 A1 | 1/2004 | Fischer et al. | |
| 2004/0102516 A1 | 5/2004 | Fischer et al. | |
| 2004/0266624 A1 | 12/2004 | Hofer | |
| 2005/0054535 A1 | 3/2005 | Fischer et al. | |
| 2005/0090399 A1 | 4/2005 | Friedmann et al. | |
| 2005/0164883 A1 | 7/2005 | Maetzke et al. | |
| 2005/0164886 A1 | 7/2005 | Glock | |
| 2006/0160847 A1 | 7/2006 | Fischer et al. | |
| 2006/0166829 A1 | 7/2006 | Fischer et al. | |
| 2007/0015664 A1 * | 1/2007 | Fischer et al. | 504/221 |
| 2007/0129252 A1 * | 6/2007 | Fischer et al. | 504/283 |
| 2007/0225167 A1 | 9/2007 | Fischer et al. | |
| 2007/0225170 A1 | 9/2007 | Fischer et al. | |
| 2008/0221167 A1 | 9/2008 | Fischer et al. | |
| 2009/0239906 A1 * | 9/2009 | Fischer et al. | 514/314 |
| 2009/0298828 A1 * | 12/2009 | Fischer et al. | 514/235.5 |
| 2010/0130578 A1 * | 5/2010 | Fischer et al. | 514/409 |
| 2011/0059991 A1 | 3/2011 | Fischer et al. | |

FOREIGN PATENT DOCUMENTS

| | | |
|---|---|---|
| CA | 2 382 432 A1 | 3/2001 |
| CA | 2 492 096 A1 | 1/2004 |
| CA | 2 497 074 A1 | 3/2004 |
| CA | 2 518 620 A1 | 9/2004 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| EP | 0 346 620 A1 | 12/1989 |
| GB | 2 266 888 A | 11/1993 |
| JP | 2000-53670 A | 2/2000 |
| WO | WO 95/07897 A1 | 3/1995 |
| WO | WO 96/02539 A1 | 2/1996 |
| WO | WO 96/11574 A1 | 4/1996 |
| WO | WO 96/21652 A1 | 7/1996 |
| WO | WO 96/25395 A1 | 8/1996 |
| WO | WO 99/16744 A1 | 4/1999 |
| WO | WO 99/43649 A1 | 9/1999 |
| WO | WO 01/17351 A1 | 3/2001 |
| WO | WO 01/17972 A2 | 3/2001 |
| WO | WO03/013249 * | 2/2003 |
| WO | WO 03/013249 A1 | 2/2003 |
| WO | WO 03/062244 A1 | 7/2003 |
| WO | WO 2004/065366 A1 | 8/2004 |
| WO | WO 2004/080962 A1 | 9/2004 |
| WO | WO 2004/111042 A1 | 12/2004 |
| WO | WO 2005/044791 A2 | 5/2005 |
| WO | WO 2005/044796 A1 | 5/2005 |
| WO | WO 2005/048710 A1 | 6/2005 |
| WO | WO 2005/049569 A1 | 6/2005 |

OTHER PUBLICATIONS

Blackshaw, R.E., "Synergistic Mixes of DPX-A7881 and Clopyralid in Canola (Brassica napus)," Weed Tech. 3:690-695, The Weed Science Society of America, United States (1989).

Blackshaw, R.E., et al, "Herbicide Combinations for Postemergent Weed Control in Safflower (Carthamus tinctorius)," Weed Tech. 4:97-104, The Weed Science Society of America, United States (1990).

Blouin, D.C., et al, "Analysis of Synergistic and Antagonistic Effects of Herbicides Using Nonlinear Mixed-Model Methodology," Weed Tech. 18:464-472, The Weed Science Society of America, United States (2004).

Bradley, P.R., et al., "Response of Sorghum (Sorghum bicolor) to Atrazine, Ammonium Sulfate, and Glyphosate," Weed Tech. 14:15-18, The Weed Science Society of America, United States (2000).

Buker, III, R.S., et al., "Confirmation and Control of a Paraquat-Tolerant Goosegrass (Eleusine indica) Biotype," Weed Tech. 16:309-313, The Weed Science Society of America, United States (2002).

Burke, I.C., et al., "CGA-362622 Antagonizes Annual Grass Control with Clethodim," Weed Tech. 16:749-754, The Weed Science Society of America, United States (2002).

Flint, J.L., et al., "Analyzing Herbicide Interactions: A Statistical Treatment of Colby's Method," Weed Tech. 2:304-309, The Weed Science Society of America, United States (1988).

Gillespie, G.R. and Nalewaja, J.D., "Wheat (Triticum aestivum) Response to Triallate Plus Chlorsulfuron," Weed Tech. 3:20-23, The Weed Science Society of America, United States (1989).

Green, J.M., et al., "Metribuzin and Chlorimuron Mixtures for Preemergence Broadleaf Weed Control in Soybeans, Glycine max, " Weed Tech. 2:355-363, The Weed Science Society of America, United States (1988).

Harker, K.N. and O'Sullivan, P.A., "Synergistic Mixtures of Sethoxydim and Fluazifop on Annual Grass Weeds," Weed Tech. 5:310-316, The Weed Science Society of America, United States (1991).

Kent, L.M., et al., "Effect of Ammonium Sulfate, Imazapyr, and Environment on the Phytotoxicity of Imazethapyr," Weed Tech. 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicdes," *Weed Tech.* 14:617-623, The Weed Science Society of America, United States (2000).

Rummens, F.H.A., "An Improved Definition of Synergistic and Antagonistic Effects," *Weed Science* 23:4-6, The Weed Science Society of America, United States (1975).

Salzman, F.P. and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E. and Allen, R.L., "Interaction of Graminicides Applied in Combination with Pyrithiobac," *Weed Tech.* 10:889-892, The Weed Science Society of America, United States (1996).

Sun, Y.-P. and Johnson, E.R., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

Office Action mailed Dec. 30, 1991, in U.S. Appl. No. 07/693,205, Krauskopf, et al., filed Apr. 30, 1991.

Office Action mailed Jul. 9, 1992, in U.S. Appl. No. 07/693,205, Krauskopf, et al., filed Apr. 30, 1991.

Office Action mailed Jun. 24, 1999, in U.S. Appl. No. 09/230,653, Lieb, et al., filed Jan. 28, 1999.

Office Action mailed Jun. 2, 2000, in U.S. Appl. No. 09/230,750, Fischer, et al., filed Feb. 1, 1999.

Office Action mailed Nov. 9, 2007, in U.S. Appl. No. 10/485,909, Fischer et al., filed Aug. 6, 2004.

Office Action mailed Mar. 13, 2009, in U.S. Appl. No. 10/542,514, Fischer et al., filed Feb. 2, 2006.

Office Action mailed Nov. 18, 2009, in U.S. Appl. No. 10/542,514, Fischer et al., filed Feb. 2, 2006.

Office Action mailed Nov. 3, 2008, in U.S. Appl. No. 10/549,074, Fischer et al., filed Feb. 21, 2006.

Office Action mailed May 20, 2009, in U.S. Appl. No. 10/549,074, Fischer et al., filed Feb. 21, 2006.

Office Action mailed Dec. 16, 2009, in U.S. Appl. No. 10/549,074, Fischer et al., filed Feb. 21, 2006.

Office Action mailed Jun. 15, 2010, in U.S. Appl. No. 10/549,074, Fischer et al., filed Feb. 21, 2006.

Office Action mailed Jan. 7, 2009, in U.S. Appl. No. 10/578,403, Fischer et al., filed Nov. 13, 2006.

Office Action mailed Aug. 3, 2009, in U.S. Appl. No. 10/578,403, Fischer et al., filed Nov. 13, 2006.

Office Action mailed Feb. 24, 2010, in U.S. Appl. No. 10/578,403, Fischer et al., filed Nov. 13, 2006.

Office Action mailed Sep. 30, 2008, in U.S. Appl. No. 10/578,900, Fischer et al., filed Mar. 8, 2007.

Office Action mailed Jun. 22, 2009, in U.S. Appl. No. 10/578,900, Fischer et al., filed Mar. 8, 2007.

Office Action mailed Jul. 17, 2009, in U.S. Appl. No. 11/901,471, Lieb et al., filed Sep. 17, 2007.

Office Action mailed Aug. 6, 2010, in U.S. Appl. No. 12/297,957, Fischer et al., filed Feb. 4, 2009.

Office Action mailed Feb. 4, 2011, in U.S. Appl. No. 12/297,957, Fischer et al., filed Feb. 4, 2009.

Office Action mailed Jun. 9, 2011, in U.S. Appl. No. 12/297,957, Fischer et al., filed Feb. 4, 2009.

Office Action mailed Jul. 20, 2010, in U.S. Appl. No. 12/303,206, Fischer et al., filed Apr. 27, 2009.

Office Action mailed Feb. 1, 2011, in U.S. Appl. No. 12/303,206, Fischer et al., filed Apr. 27, 2009.

Office Action mailed Jul. 19, 2011, in U.S. Appl. No. 12/303,206, Fischer et al., filed Apr. 27, 2009.

Berenbaum, M.C., "What is Synergy?" *Pharmacol. Rev.* 1989(41):93-141, The American Society for Pharmacology and Experimental Therapeutics, United States (1989).

Office Action mailed Aug. 9, 2011, in U.S. Appl. No. 12/297,957, Fischer et al., filed Feb. 4, 2009.

Office Action mailed Nov. 26, 1993, in U.S. Appl. No. 08/024,202, Iwata et al., filed Feb. 23, 1993.

Office Action mailed Aug. 22, 1994, in U.S. Appl. No. 08/024,202, Iwata et al., filed Feb. 23, 1993.

Campbell, A.C., et al., "Synthesis of (E)- and (Z)-Pulvinones," *J. Chem. Soc. Perkin Trans.* I:1567-1576, RSC Publishing (1985).

Chirazi, A.M., et al., "Syntheses of Heterocycles, 184: The Synthesis of Kawalactone Derivatives," *Arch. Pharm.* 309:558-564, Verlag Chemie GmbH (1976).

Colby, S.R., "Calculating Synergistic and Antagonistic Responses of Herbicide Combinations," *Weeds* 15:20-22, Weed Society of America (1967).

Edwards, R.L., et al., "Constituents of the Higher Fungi. Part IV. Involutin, a Diphenylcyclopenteneone from *Paxillus involutus* (Oeder ex Fries)," *J. Chem. Soc.* C:405-409, RSC Publishing (1967).

Ketcham, R., et al., "Synthesis of Heterocycles. 174 (1,2) Substituted Thiazines and Bisthiazinyls from Dithiooxamide and Trichlorophenyl Malonates," *J. Heterocycl. Chem.* 10:223-224, Journal of Heterocyclic Chemistry (1973).

Micklefield, J., et al., "Alkylation and Acylation of 5-Phenylsulphonyl- and 5-Cyanobutyrolactones," *Tetrahedron* 48:7519-7526, Pergamon Press (1992).

Schmierer, R. and Mildenberger, H., "Cyclisierung von N-Acylalanin- and N-Acylglycinestern," *Liebigs Ann. Chem.* 1985:1095-1098, VCH Verlagsgesellschaft mbH (1985).

Suzuki, S., et al., "Studies on Antiviral Agents. IV. Biological Activity of Tenuazonic Acid Derivatives," *Chem. Pharm. Bull.* 15:1120-1122, Pharmaceutical Society of Japan (1967).

Sousa, A.A., et al., "Esters of 3-Hydroxy-2-Arylindones, a New Class of Acaricide," *J. Economic Entomology* 66:584-586, Entomological Society of America (1973).

Wheeler, T.N., "Novel Photochemical Synthesis of 2-Aryl-1,3-cyclohexanediones," *J. Org. Chem.* 44:4906-4912, American Chemical Society (1979).

International Search Report for International Application No. PCT/EP2005/007794, mailed on Nov. 9, 2005, European Patent Office, Netherlands.

Dialog File 351, Accession No. 4963457, Derwent WPI English language abstract for EP 0 346 620 A1 (listed on accompanying PTO/SB/08A as document FP1), Dec. 20, 1989.

Patent Abstracts of Japan, English language abstract for JP 2000-53670 A (listed on accompanying PTO/SB/08A as document FP8), 2000.

\* cited by examiner

SELECTIVE INSECTICIDES BASED ON SUBSTITUTED CYCLIC KETOENOLS AND SAFENERS

This application is a National Stage of International Application No. PCT/EP2005/007794, filed Jul. 18, 2005, which claims the benefit of German Patent Application No. 10 2004 035 133.3, filed Jul. 20, 2004. The entirety of each of these applications is incorporated by reference herein.

The invention relates to the use of selective insecticidally and/or acaricidally active compound combinations which comprise substituted cyclic ketoenols, on the one hand, and at least one compound which improves crop plant compatibility, on the other, for the selective control of insects and/or spider mites in various crops of useful plants.

Pharmaceutical properties of 3-acylpyrrolidine-2,4-diones have already been described (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal action has been disclosed. Unsubstituted bicyclic 3-arylpyrrolidine-2,4-dione derivatives (EP-A-355 599, EP-A-415 211 and JP 12-053 670) and substituted monocyclic 3-arylpyrrolidine-2,4-dione derivatives (EP-A-377 893 and EP-A-442 077) having herbicidal, insecticidal or acaricidal action have been disclosed.

There have also been disclosed polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 und WO 99/55673, WO 01/17972, WO 01/23354, WO 01/74770, WO 03/062244, WO 04/007448, WO 04/024688, WO 04/080962, WO 04/065366, WO 04/111042, DE-A-10351646, DE-A-10354628, DE-A-10354629, DE-A-10351647).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-2-one) is also described in DE-A-4 014 420. Compounds of a similar structure known from the publication Campbell et al., J. Chem. Soc., Perkin Trans. 1, 1985, (8) 1567-76, but no insecticidal and/or acaricidal activity is mentioned. 3-Aryl-$\Delta^3$-dihydrofuranone derivatives having herbicidal, acaricidal and insecticidal properties are also known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/23354, WO 01/74770, WO 03/062244, WO 04/024688 and WO 04/080962. 3-Aryl-$\Delta^3$-dihydrothiophenone derivatives are likewise known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/062244, WO 04/080962, WO 04/111042).

Certain phenylpyrone derivatives which are unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849), but a possible use of these compounds as pesticides has not been mentioned. Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/062244, WO 04/080962, WO 04/111042.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)), but a possible use of these compounds as pesticides has not been mentioned. 5-Phenyl-1,3-thiazine derivatives which are substituted in the phenyl ring and have herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972, WO 01/74770, WO 03/062244, WO 04/080962, WO 04/111042.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/062244, WO 04/080962, WO 04/111042). Moreover, compounds having similar substitutions are known; 3-hydroxy-5,5-dimethyl-2-phenylcyclopent-2-en-1-one from the publication Micklefield et al., Tetrahedron, (1992), 7519-26, and the natural product involution (−)-cis-5-(3,4-dihydroxyphenyl)-3,4-dihydroxy-2-(4-hydroxyphenyl)cyclopent-2-en one from the publication Edwards et al., J. Chem. Soc. S, (1967), 405-9. An insecticidal or acaricidal action is not described. Moreover, 2-(2,4,6-tri-methylphenyl)-1,3-indanedione is known from the publication J. Economic Entomology, 66, (1973), 584 and the Offenlegungsschrift (German Published Specification) DE-A 2 361 084, with herbicidal and acaricidal actions being mentioned.

It is known that certain substituted 2-arylcyclohexanediones have herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979), WO 99/43649, WO 99/48869, WO 99/55673, WO 01/17972, WO 01/74770, WO 03/062244, WO 04/080962, WO 04/111042).

It is known that certain substituted 4-arylpyrazolidine-3,5-diones have acaricidal, insecticidal and herbicidal properties (cf., for example, WO 92/16 510, EP-A-508 126, WO 96/11 574, WO 96/21 652, WO 99/47525, WO 01/17 351, WO 01/17 352, WO 01/17 353, WO 01/17 972, WO 01/17 973, WO 03/028466, WO 03/062244, WO 03/062244, WO 04/080962).

Moreover, selective herbicides based on substituted cyclic ketoenols and safeners have been described (WO 03/013249).

However, the compatibility of these compounds in particular with monocotyledonous crop plants is not under all conditions entirely satisfactory.

Surprisingly, it has now been found that certain substituted cyclic ketoenols, when used together with the crop plant compatibility-improving compounds (safeners/antidotes)

described below, prevent damage to the crop plants extremely efficiently and can be used particularly advantageously as broadband combination preparations for the selective control of insects even in crops of monocotyledonous useful plants, such as, for example, in cereals, but also in maize, millet and rice.

The invention provides the use of selective insecticidal and/or acaricidal compositions comprising an effective amount of an active compound combination comprising, as components, (a) at least one substituted cyclic ketoenol of the formula (I)

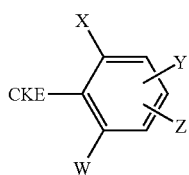
(I)

in which

X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro or cyano, Z represents hydrogen, alkyl, halogen, alkenyl, alkynyl, represents in each case optionally substituted aryl or hetaryl, W and Y independently of one another represent hydrogen, halogen, alkyl, alkoxy, alkenyloxy, haloalkyl, haloalkoxy, haloalkenyloxy, nitro or cyano, CKE represents one of the groups

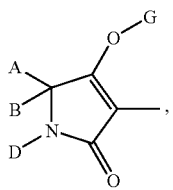
(1)

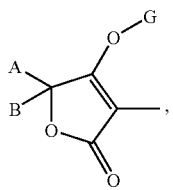
(2)

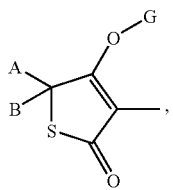
(3)

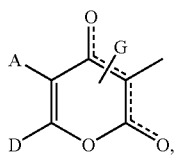
(4)

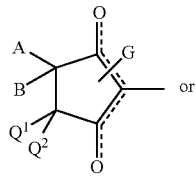
(5)

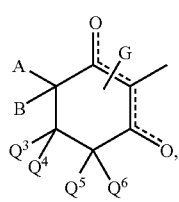
(6)

in which

A represents hydrogen, in each case optionally halogen-substituted alkyl, alkenyl, alkoxyalkyl, alkylthioalkyl, saturated or unsaturated, optionally substituted cycloalkyl, in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl, in which optionally one or more ring members are replaced by heteroatoms, arylalkyl, aryl, hetarylalkyl or hetaryl, or A and D together with the atoms to which they are attached represent a saturated or unsaturated cycle which is unsubstituted or substituted in the A,D moiety and optionally contains at least one heteroatom, or A and $Q^1$ together represent alkanediyl or alkenediyl which are in each case optionally substituted by hydroxyl or by in each case optionally substituted alkyl, alkoxy, alkylthio, cycloalkyl, benzyloxy or aryl, or $Q^1$ represents hydrogen or alkyl, $Q^2$, $Q^4$, $Q^5$ and $Q^6$ independently of one another represent hydrogen or alkyl, $Q^3$ represents hydrogen, alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached, represent a saturated or unsaturated, unsubstituted or substituted cycle which optionally contains a heteroatom, G represents hydrogen (a) or represents one of the groups

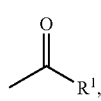
(b)

-continued

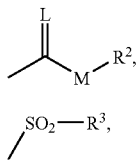
(c)

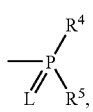
(d)

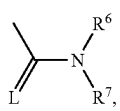
(e)

E   (f)

(g)

in which
E represents a metal ion equivalent or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl, which may be interrupted by at least one heteroatom, represents in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio,
$R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur,
including all possible tautomeric forms of the compounds of the general formula (I) and the possible salts or acid or base adducts of the compounds of the general formula (I)—
and
(b) at least one crop plant compatibility-improving compound, from the group of compounds below:
4-dichloroacetyl-1-oxa-4-aza-spiro[4.5]-decane (AD-67, MON-4660), 1-di-chloroacetyl-hexahydro-3,3,8a-trimethylpyrrolo[1,2-a]-pyrimidin-6(2H)-one (di-cyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate(cloquintocet-mexyl—cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyanomethoximino)-phenylacetonitrile (cyometrinil), 2,4-dichlorophenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazole-ethyl—cf. also related compounds in EP-A-174562 and EP-A-346620), phenyl-methyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)-ethyl 3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-aza-spiro[4.5]decane 4-carbodithioate (MG-838), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chlorophenoxy)-butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf. also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinoxalin-8-oxy-acetate, ethyl 5-chloro-quinolin-8-oxy-acetate, allyl 5-chloro-quinoxalin-8-oxy-acetate, 2-oxo-prop-1-yl 5-chloro-quinolin-8-oxy-acetate, diethyl 5-chloro-quinolin-8-oxy-malonate, diallyl 5-chloro-quinoxalin-8-oxy-malonate, diethyl 5-chloro-quinolin-8-oxy-malonate (cf. also related compounds in EP-A-582198), 4-carboxy-chroman-4-yl-acetic acid (AC-304415, cf. EP-A-613618), 4-chloro-phenoxy-acetic acid, 3,3'-dimethyl-4-methoxy-benzophenone, 1-bromo-4-chloromethylsulphonyl-benzene, 1-[4-(N-2-methoxybenzoylsulphamoyl)-phenyl]-3-methyl-urea (alias N-(2-methoxy-benzoyl)-4-[(methylamino-carbonyl)-amino]-benzenesulphonamide), 1-[4-(N-2-methoxy-benzoylsulphamoyl)-phenyl]-3,3-dimethyl-urea, 1-[4-(N-4,5-dimethylbenzoyl-sulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropylaminocarbonyl)-benzenesulphonamide, and/or one of the following compounds defined by general formulae of the general formula (IIa)

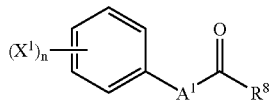
(IIa)

or of the general formula (IIb)

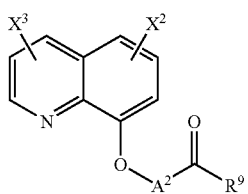
(IIb)

or the formula (IIc)

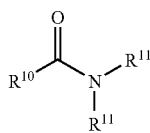
(IIc)

where
m represents a number 0, 1, 2, 3, 4 or 5,
$A^1$ represents one of the divalent heterocyclic groupings shown below

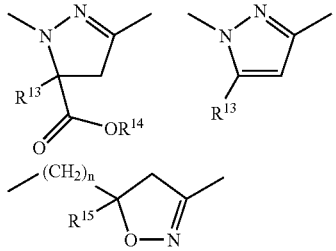

n represents a number 0, 1, 2, 3, 4 or 5,
$A^2$ represents optionally $C_1$-$C_4$-alkyl- and/or $C_1$-$C_4$-alkoxy-carbonyl- and/or $C_1$-$C_4$-alkenyloxycarbonyl-substituted alkanediyl with 1 or 2 carbon atoms,
$R^8$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino,
$R^9$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl)-amino,
$R^{10}$ represents in each case optionally fluorine-, chlorine- and/or bromine-substituted $C_1$-$C_4$-alkyl,
$R^{11}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl,
$R^{12}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or $R^{11}$ and $R^{12}$ together also represent $C_3$-$C_6$-alkanediyl or $C_2$-$C_5$-oxaalkanediyl, each of which is optionally substituted by $C_1$-$C_4$-alkyl, phenyl, furyl, a fused-on benzene ring or by two substituents which together with the C atom to which they are attached form a 5- or 6-membered carbocycle,
$R^{13}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$R^{14}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl,
$R^{15}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl,
$X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy,
$X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
$X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy,
and/or the following compounds defined by general formulae of the general formula (IId)

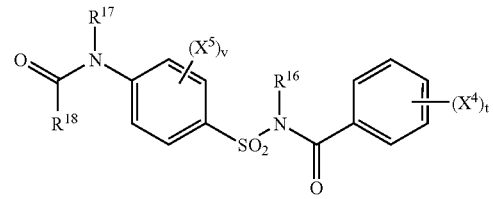
(IId)

or of the general formula (IIe)

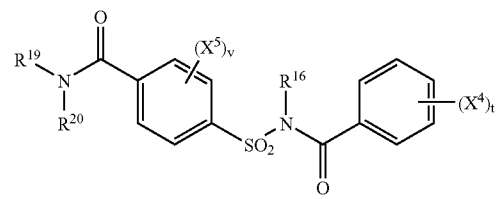
(IIe)

where
t represents a number 0, 1, 2, 3, 4 and 5,
v represents a number 0, 1, 2, 3, 4 and 5,
$R^{16}$ represents hydrogen or $C_1$-$C_4$-alkyl,
$R^{17}$ represents hydrogen or $C_1$-$C_4$-alkyl,
$R^{18}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)-amino, or in each case optionally cyano-, halogenor $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{19}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{20}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{19}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, for controlling insects and/or arachnids.

In the definitions, the hydrocarbon chains, such as in alkyl or alkanediyl, are in each case straight-chain or branched—including in combination with heteroatoms, such as in alkoxy.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, and their use and the compositions comprising them. However, for the sake of simplicity, hereinbelow only compounds of the formula ) are referred to, although what is meant are both the pure compounds and, if appropriate, also mixtures having various proportions of isomeric compounds.

Including the meanings (1) to (6) of the group CKE, the following principal structures (I-1) to (I-6) result:

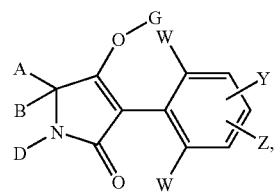
(I-1)

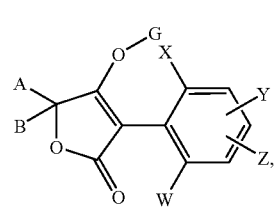
(I-2)

-continued

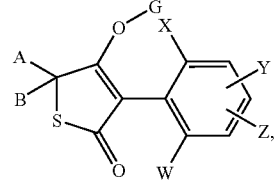
(I-3)

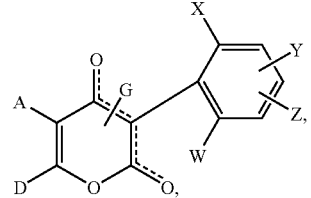
(I-4)

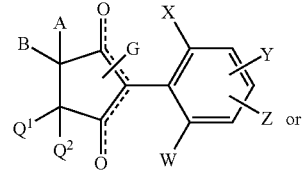
(I-5)

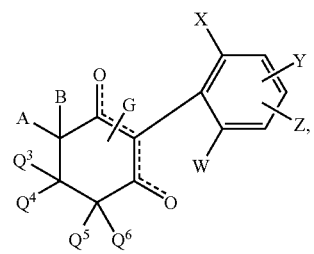
(I-6)

in which
A, B, D, G, $Q^1$, $Q^2$, $Q^3$, $Q^4$, $Q^5$, $Q^6$, W, X, Y and Z are as defined above.

Including the different meanings (a), (b), (c), (d), (e), (f) and (g) of the group G, the following principal structures (I-1-a) to (I-1-g) result if CKE represents the group (1),

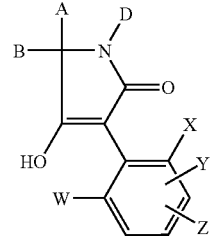
(I-1-a)

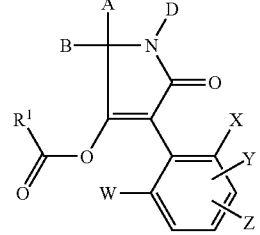
(I-1-b)

-continued
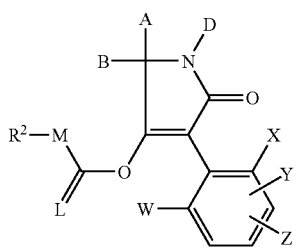
(I-1-c)
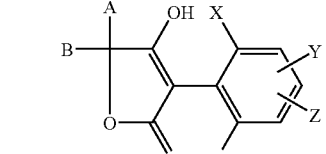
(I-2-a)
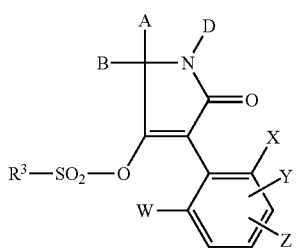
(I-1-d)
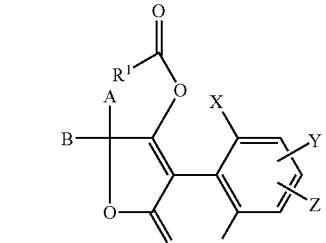
(I-2-b)
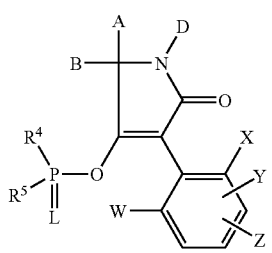
(I-1-e)
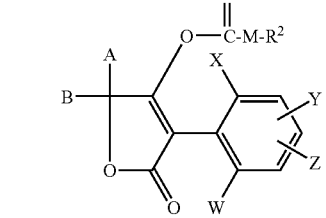
(I-2-c)
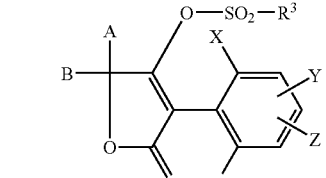
(I-2-d)
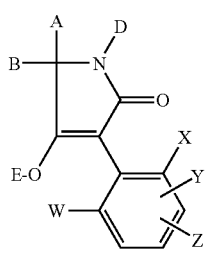
(I-1-f)
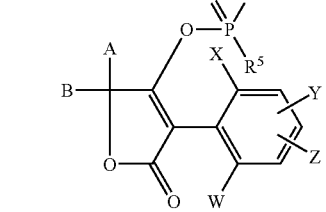
(I-2-e)
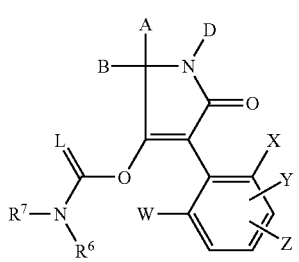
(I-1-g)
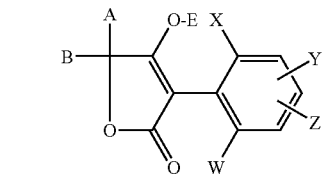
(I-2-f)
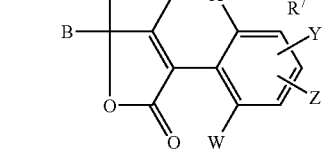
(I-2-g)
in which
A, B, D, E, L, M, W, X, Y, Z, $R^1$, $R^2$, $R^3$, $R^4$, $R^5$, $R^6$ and $R^7$ are as defined above.
Including the different meanings (a), (b), (c), (d), (e), (f) and (g) of the group G, the following principal structures (I-2-a) to (I-2-g) result if CKE represents the group (2)

in which
A, B, E, L, M, W, X, Y, Z, $R^1$, $R^2$, $R^3$, $R^4$, $R^5$, $R^6$ and $R^7$ are as defined above.

Including the different meanings (a), (b), (c), (d), (e), (f) and (g) of the group G, the following principal structures (I-3-a) to (I-3-g) result if CKE represents the group (3)

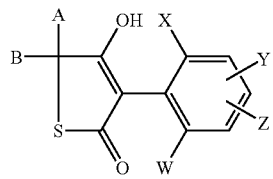
(I-3-a)

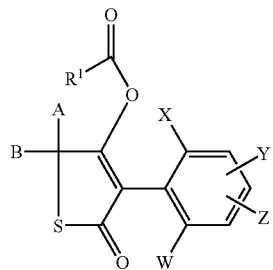
(I-3-b)

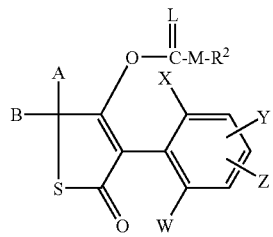
(I-3-c)

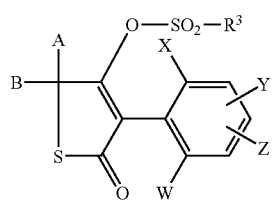
(I-3-d)

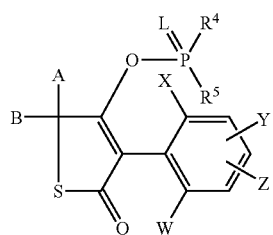
(I-3-e)

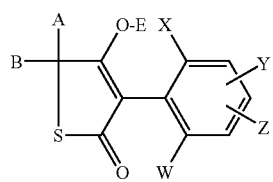
(I-3-f)

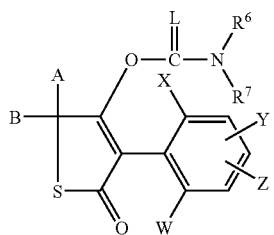
(I-3-g)

in which
A, B, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-4) can be present in the two isomeric forms of the formulae (I-4-A) and (I-4-B)

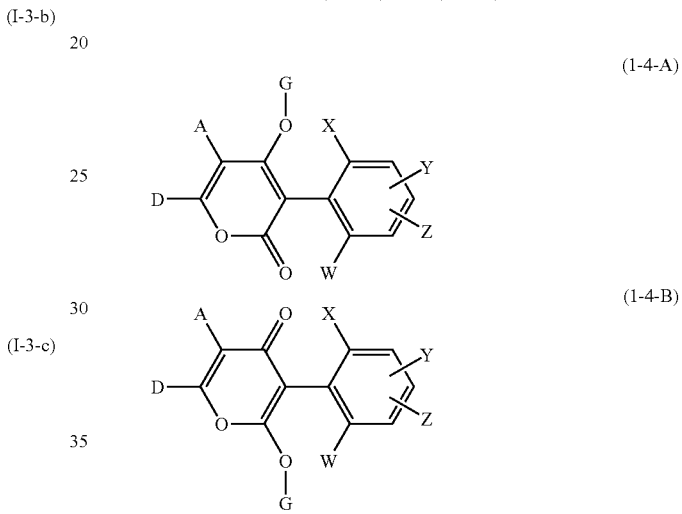

(1-4-A)

(1-4-B)

which is meant to be indicated by the broken line in formula (I-4).

The compounds of the formulae (I-4-A) and (I-4-B) can be present both as mixtures and in the form of their pure isomers. Mixtures of the compounds of the formulae (I-4-A) and (I-4-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Including the different meanings (a), (b), (c), (d), (e), (f) and (g) of the group G, the following principal structures (I-4-a) to (I-4-g) result if CKE represents the group (4)

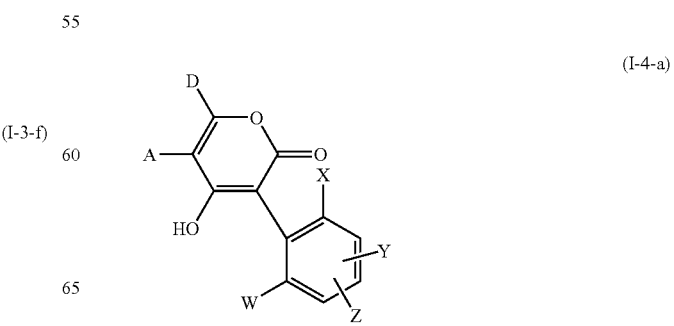
(I-4-a)

-continued

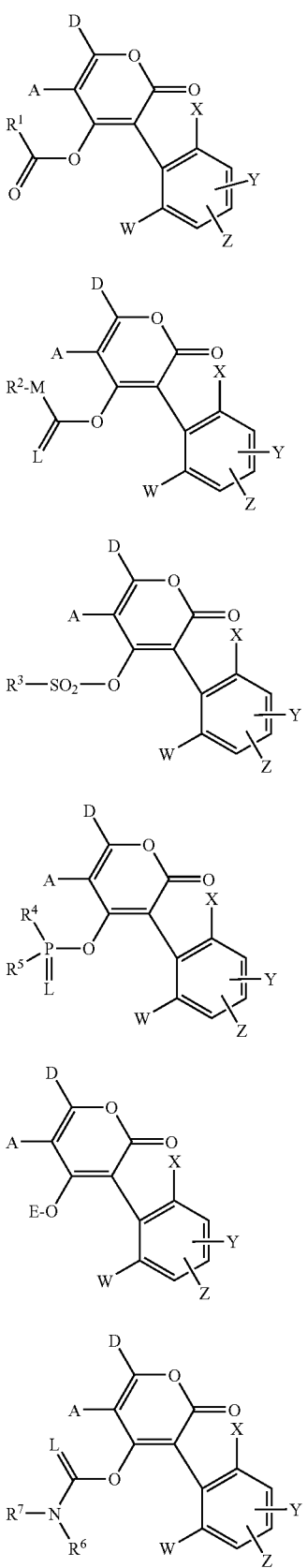

(I-4-b)
(I-4-c)
(I-4-d)
(I-4-e)
(I-4-f)
(I-4-g)

in which

A, D, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-5) can be present in the two isomeric forms of the formulae (I-5-A) and (I-5-B)

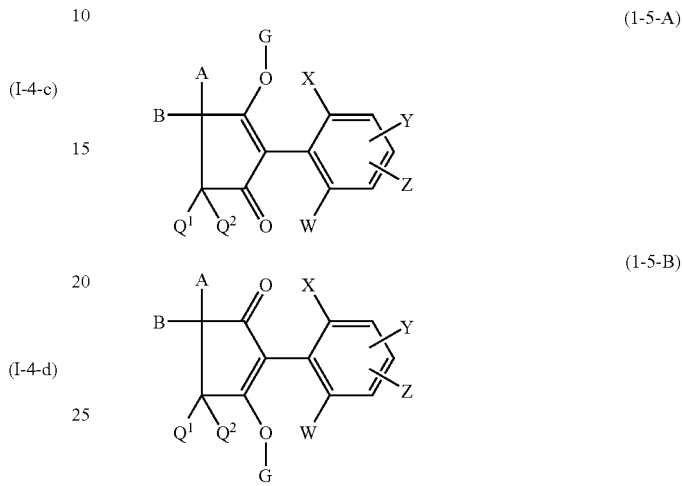

(I-5-A)

(I-5-B)

which is meant to be indicated by the broken line in the formula (I-5).

The compounds of the formulae (I-5-A) and (I-5-B) can be present both as mixtures and in the form of their pure isomers. Mixtures of the compounds of the formulae (I-5-A) and (I-5-B) can, if appropriate, be separated by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Including the different meanings (a), (b), (c), (d), (e), (f) and (g) of the group G, the following principal structures (I-5-a) to (I-5-g) result:

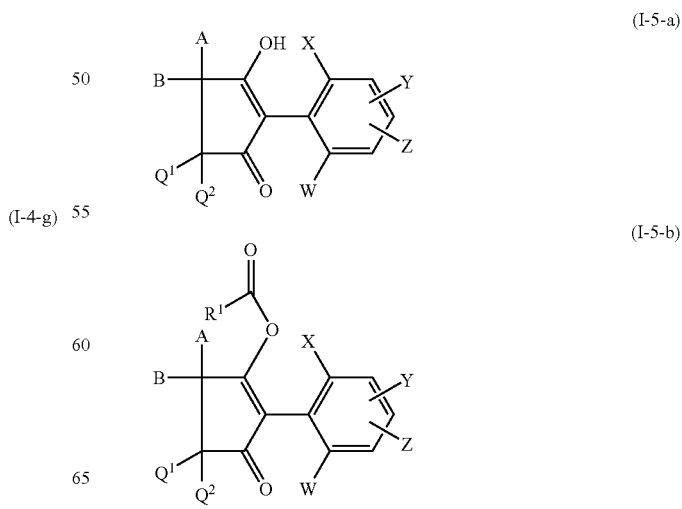

(I-5-a)

(I-5-b)

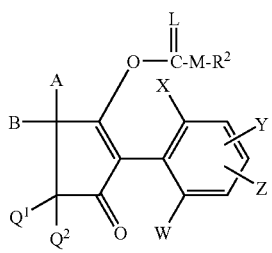
(I-5-c)

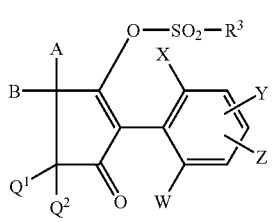
(I-5-d)

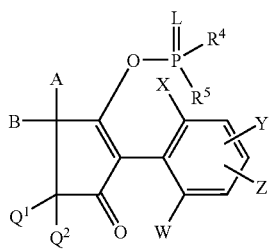
(I-5-e)

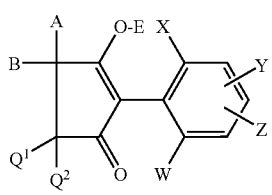
(I-5-f)

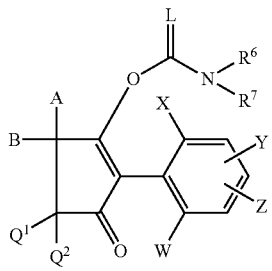
(I-5-g)

in which
A, B, $Q^1$, $Q^2$, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B) which is meant to be indicated by the broken line in the formula (I-6):

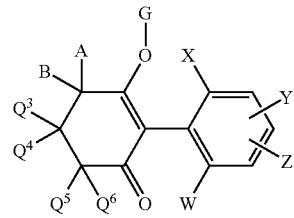
(1-6-A)

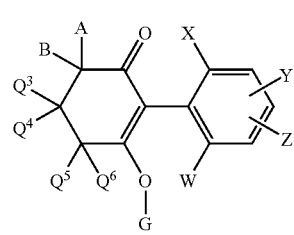
(1-6-B)

The compounds of the formulae (I-6-A) and (I-6-B) can be present both as mixtures and in the form of their pure isomers. Mixtures of the compounds of the formulae (I-6-A) and (I-6-B) may, if appropriate, be separated by physical methods, for example by chromatographic methods.

For reasons of clarity, hereinbelow only one of the possible isomers is shown in each case. This includes that the compound in question may, if appropriate, be present as an isomer mixture or in the respective other isomeric form.

Including the different meanings (a), (b), (c), (d), (e), (f) and (g) of the group G, the following principal structures (I-6-a) to (I-6-g) result:

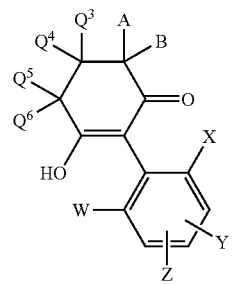
(I-6-a)

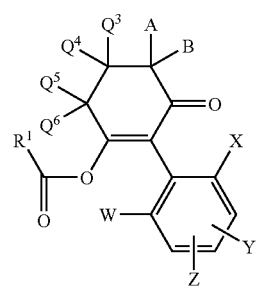
(I-6-b)

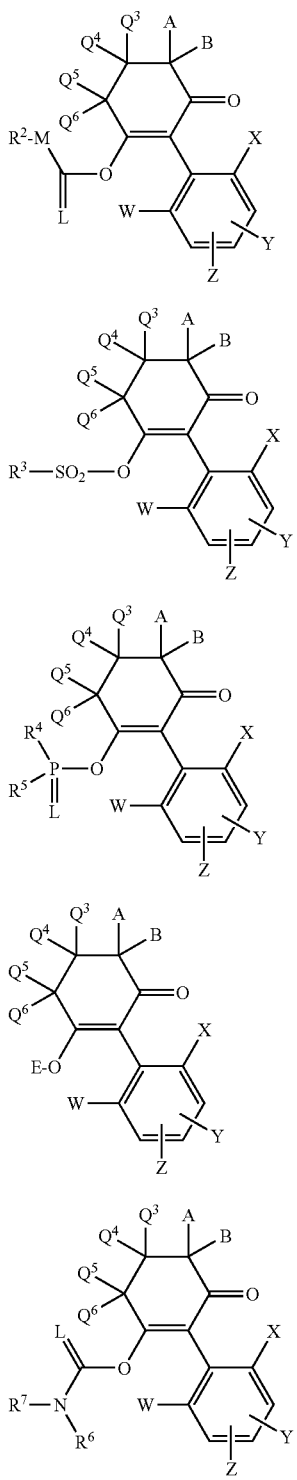

(I-6-c)

(I-6-d)

(I-6-e)

(I-6-f)

(I-6-g)

in which
A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are as defined above.

The formula (I) provides a general definition of the substituted cyclic ketoenols according to the invention of the acaricidal and insecticidal compositions. Preferred substituents and ranges of the radicals given in the formulae mentioned above and below are illustrated below:

X preferably represents halogen, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_6$-alkenyloxy, $C_1$-$C_6$-haloalkoxy, $C_3$-$C_6$-haloalkenyloxy, nitro or cyano, Z preferably represents hydrogen, halogen, $C_1$-$C_6$-alkyl, $C_2$-$C_6$-alkenyl, $C_2$-$C_6$-alkynyl or represents one of the radicals

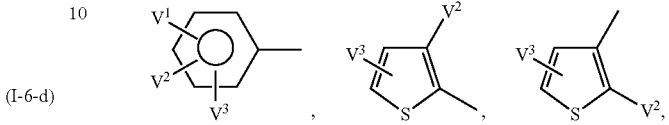

in which
$V^1$ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, W and Y independently of one another preferably represent hydrogen, halogen, $C_1$-$C_6$-alkyl, $C_1$-$C_6$-haloalkyl, $C_1$-$C_6$-alkoxy, $C_1$-$C_6$-haloalkoxy, nitro or cyano, CKE preferably represents one of the groups

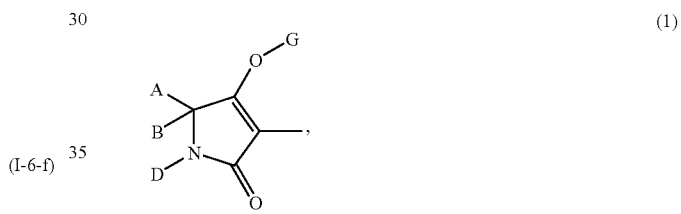 (1)

 (2)

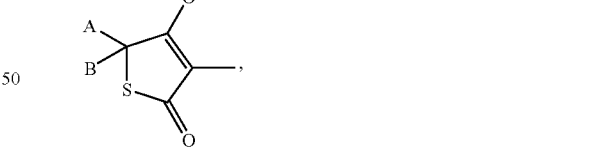 (3)

 (4)

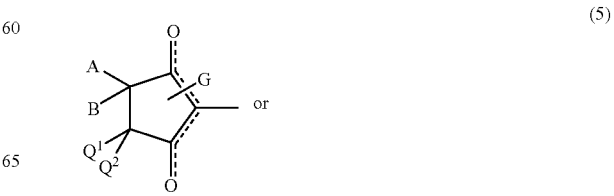 (5)

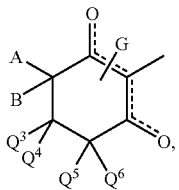
(6)

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or phenyl-$C_1$-$C_6$-alkyl, B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen or phenyl, or A, B and the carbon atom to which they are attached preferably represent $C_5$-$C_6$-cycloalkyl which is substituted by an alkylenediyl or by an alkylenedioxyl or by an alkylenedithiol group which, with the carbon atom to which it is attached, forms a further 5- to 8-membered ring and which is optionally substituted by $C_1$-$C_4$-alkyl which optionally contains one or two not directly adjacent oxygen and/or sulphur atoms, or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanediendiyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or phenyl-$C_1$-$C_6$-alkyl, or A and D together preferably represent in each case optionally substituted $C_3$-$C_6$-alkanediyl or $C_3$-$C_6$-alkenediyl in which optionally one methylene group is replaced by a carbonyl group, by oxygen or by sulphur, and possible substituents being in each case:
halogen, hydroxyl, mercapto or in each case optionally halogen-substituted $C_1$-$C_{10}$-alkyl or $C_1$-$C_6$-alkoxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compounds of the formula (I-1), A and D together with the atoms to which they are attached then represent, for example, the groups AD-1 to AD-10 mentioned further below), which may contain oxygen or sulphur, A and $Q^1$ together preferably represent $C_3$-$C_6$-alkanediyl or $C_4$-$C_6$-alkenediyl, each of which is optionally mono- or disubstituted by identical or different halogens, by $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogens, or by benzyloxy or phenyl, each of which is optionally mono- to trisubstituted by identical or different substituents from the group consisting of halogen, $C_1$-$C_6$-alkyl and $C_1$-$C_6$-alkoxy, where the $C_3$-$C_6$-alkanediyl or $C_4$-$C_6$-alkenediyl is furthermore bridged by a $C_1$-$C_2$-alkanediyl group or by an oxygen atom, or $Q^1$ preferably represents hydrogen or $C_1$-$C_4$-alkyl, $Q^2$, $Q^4$, $Q^5$ and $Q^6$ independently of one another preferably represent hydrogen or $C_1$-$C_4$-alkyl, $Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur or represents optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^3$ and $Q^4$ together with the carbon atom to which they are attached preferably represent an optionally $C_1$-$C_4$-alkyl-, $C_1$-$C_4$-alkoxy- or $C_1$-$C_2$-haloalkyl-substituted $C_3$-$C_7$-ring in which optionally one ring atom is replaced by oxygen or sulphur, G preferably represents hydrogen (a) or represents one of the groups

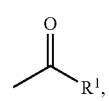
(b)

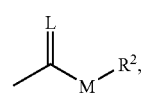
(c)

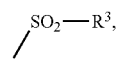
(d)

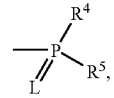
(e)

E or
(f)

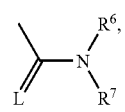
(g)

in particular (a), (b), (c) or (g),
in which
E represents a metal ion equivalent or an ammonium ion,
L represents oxygen or sulphur and
M represents oxygen or sulphur,
$R^1$ preferably represents in each case optionally halogen-substituted $C_1$-$C_{20}$-alkyl, $C_2$-$C_{20}$-alkenyl, $C_1$-$C_8$-alkoxy- $C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl, $C_1$-$C_6$-alkoxy-, $C_1$-$C_6$-haloalkyl- or $C_1$-$C_6$-haloalkoxy substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_9$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur.

In the radical definitions mentioned as being preferred, halogen represents fluoroine, chlorine, bromine and iodine, in particular fluorine, chlorine and bromine.

X particularly preferably represents fluorine, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl, $C_1$-$C_4$-haloalkoxy or cyano, Z particularly preferably represents hydrogen, fluorine, chlorine, bromine, $C_1$-$C_4$-alkyl, $C_2$-$C_4$-alkenyl, $C_2$-$C_4$-alkynyl or represents the radical

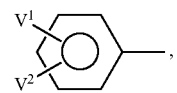

$V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro or cyano, $V^2$ particularly preferably represents hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, W and Y independently of one another particularly preferably represent hydrogen, fluorine, chlorine, bromine, $C_1$-$C_4$-alkyl, $C_1$-$C_4$-haloalkyl, $C_1$-$C_4$-alkoxy or $C_1$-$C_4$-haloalkoxy, CKE particularly preferably represents one of the groups (1)
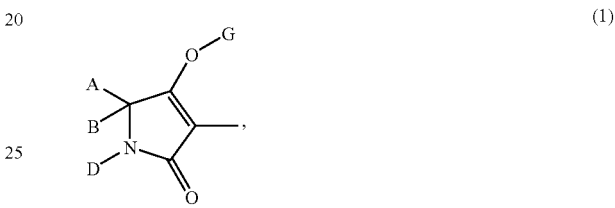

(2)
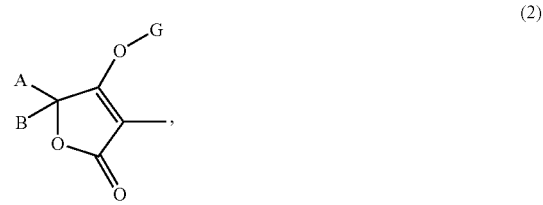

(3)
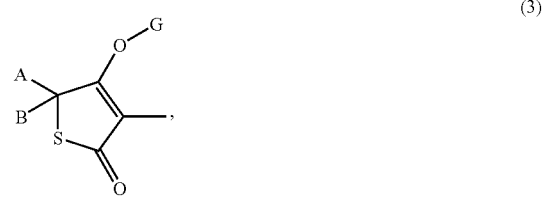

(4)
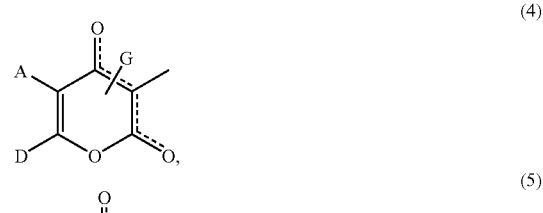

(5)
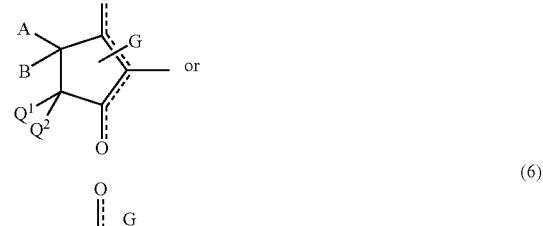
or (6)

A particularly preferably represents hydrogen, in each case optionally fluorine- or chlorine-substituted $C_1$-$C_6$-alkyl, $C_1$-$C_4$-alkoxy-$C_1$-$C_4$-alkyl or optionally fluorine-, chlorine-, $C_1$-$C_4$-alkyl- or $C_1$-$C_4$-alkoxy-substituted $C_3$-$C_7$-cycloalkyl, B particularly preferably represents hydrogen or $C_1$-$C_6$-alkyl, or A, B and the carbon atom to which they are attached particularly preferably represent saturated $C_3$-$C_7$-cycloalkyl or unsaturated $C_5$-$C_7$-cycloalkyl in which optionally one ring member is replaced by oxygen or sulphur and which is optionally monosubstituted by $C_1$-$C_6$-alkyl, $C_1$-$C_3$-haloalkyl or $C_1$-$C_6$-alkoxy, or A, B and the carbon atom to which they are attached particularly preferably represent $C_5$-$C_6$-cycloalkyl which is substituted by an alkylenediyl or by an alkylenedioxy or by an alkylenedithiol group which, together with the carbon atom to which it is attached, forms a further five- or six-membered ring and which is optionally substituted by methyl or ethyl and optionally contains one or two not directly adjacent oxygen or sulphur atoms, D particularly preferably represents hydrogen, represents in each case optionally fluorine- or chlorine-substituted $C_1$-$C_6$-alkyl, $C_3$-$C_6$-alkenyl, $C_1$-$C_4$-alkoxy-$C_2$-$C_3$-alkyl, represents optionally $C_1$-$C_4$-alkyl-, $C_1$-$C_4$-alkoxy- or $C_1$-$C_2$-haloalkyl-substituted $C_3$-$C_7$-cycloalkyl, or A and D together particularly preferably represent optionally substituted $C_3$-$C_5$-alkanediyl in which one methylene group may be replaced by oxygen or sulphur, possible substituents being $C_1$-$C_4$-alkyl, or A and D (in the case of the compounds of the formula (I-1)) together with the atoms to which they are attached represent one of the groups AD-1 to AD-10:

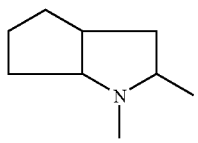

AD-1

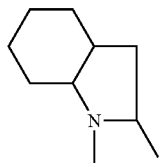

AD-2

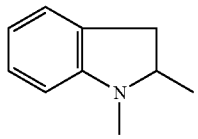

AD-3

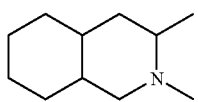

AD-4

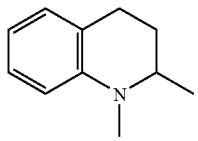

AD-5

-continued

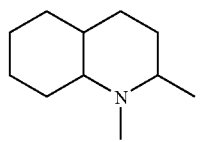

AD-6

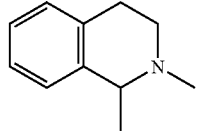

AD-7

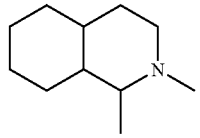

AD-8

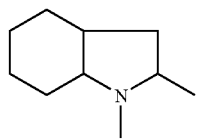

AD-9

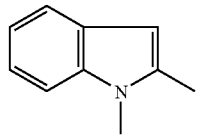

AD-10

A and $Q^1$ together particularly preferably represent $C_3$-$C_4$-alkanediyl or $C_3$-$C_4$-alkenediyl, each of which is optionally mono- or disubstituted by identical or different substituents from the group consisting of $C_1$-$C_4$-alkyl and $C_1$-$C_4$-alkoxy, or $Q^1$ particularly preferably represents hydrogen, $Q^2$ particularly preferably represents hydrogen, $Q^4$, $Q^5$ and $Q^6$ independently of one another particularly preferably represent hydrogen or $C_1$-$C_2$-alkyl, $Q^3$ particularly preferably represents hydrogen, $C_1$-$C_4$-alkyl, $C_1$-$C_4$-alkoxy-$C_1$-$C_2$-alkyl, $C_1$-$C_4$-alkylthio-$C_1$-$C_2$-alkyl or optionally methyl- or methoxy-substituted $C_3$-$C_6$-cycloalkyl in which optionally one methylene group is replaced by oxygen or sulphur, or $Q^3$ and $Q^4$ together with the carbon to which they are attached particularly preferably represent an optionally $C_1$-$C_4$-alkyl- or $C_1$-$C_4$-alkoxy-substituted saturated $C_5$-$C_6$-ring in which optionally one ring member is replaced by oxygen or sulphur, G particularly preferably represents hydrogen (a) or represents one of the groups (b)

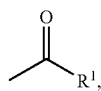

(c)

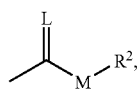

(d)

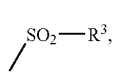

-continued

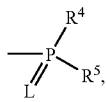
E or

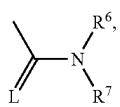

in particular (a), (b) or (c),
in which
E represents a metal ion equivalent or an ammonium ion,
L represents oxygen or sulphur and
M represents oxygen or sulphur, $R^1$ particularly preferably represents in each case optionally fluorine- or chlorine-substituted $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_6$-alkyl or optionally fluorine-, chlorine-, $C_1$-$C_4$-alkyl- or $C_1$-$C_4$-alkoxy-substituted $C_3$-$C_7$-cycloalkyl in which optionally one or two not directly adjacent ring members are replaced by oxygen and/or sulphur, represents optionally fluorine-, chlorine-, bromine-, cyano-, nitro-, $C_1$-$C_4$-alkyl-, $C_1$-$C_4$-alkoxy-, $C_1$-$C_3$-haloalkyl- or $C_1$-$C_3$-haloalkoxy-substituted phenyl, $R^2$ particularly preferably represents in each case optionally fluorine-substituted $C_1$-$C_{16}$-alkyl, $C_2$-$C_{16}$-alkenyl or $C_1$-$C_6$-alkoxy-$C_2$-$C_6$-alkyl,
represents optionally fluorine-, chlorine-, $C_1$-$C_4$-alkyl- or $C_1$-$C_4$-alkoxy-substituted $C_3$-$C_7$-cycloalkyl,
represents in each case optionally fluorine-, chlorine-, bromine-, cyano-, nitro-, $C_1$-$C_4$-alkyl-$C_1$-$C_3$-alkoxy-, $C_1$-$C_3$-haloalkyl- or $C_1$-$C_3$-haloalkoxy-substituted phenyl or benzyl, $R^3$ particularly preferably represents optionally fluorine-substituted $C_1$-$C_6$-alkyl or represents optionally fluorine-, chlorine-, bromine-, $C_1$-$C_4$-alkyl-, $C_1$-$C_4$-alkoxy-, $C_1$-$C_3$-haloalkyl-, $C_1$-$C_3$-haloalkoxy-, cyano- or nitro-substituted phenyl, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents in each case optionally fluorine-, chlorine-, bromine-, nitro-, cyano-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkyl- or $C_1$-$C_3$-haloalkyl-substituted phenyl, phenoxy or phenylthio, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents optionally fluorine-, chlorine-, bromine-, $C_1$-$C_3$-haloalkyl-, $C_1$-$C_4$-alkyl- or $C_1$-$C_4$-alkoxy-substituted phenyl, represents optionally fluorine-, chlorine-, bromine-, $C_1$-$C_4$-alkyl-, $C_1$-$C_3$-haloalkyl- or $C_1$-$C_4$-alkoxy-substituted benzyl, $R^7$ particularly preferably represents $C_1$-$C_6$-alkyl, $C_3$-$C_6$-alkenyl or $C_1$-$C_6$-alkoxy-$C_1$-$C_4$-alkyl, or $R^6$ and $R^7$ together particularly preferably represent an optionally methyl- or ethyl-substituted $C_4$-$C_5$-alkylene radical in which optionally one methylene group is replaced by oxygen or sulphur.

In the radical definitions mentioned as being particularly preferred, halogen represents fluorine, chlorine, bromine and iodine, in particular fluorine, chlorine and bromine.

W very particularly preferably represents hydrogen, chlorine, bromine, methyl, ethyl or methoxy, X very particularly preferably represents chlorine, bromine, methyl, ethyl, methoxy, ethoxy or trifluoromethyl, Y very particularly preferably represents hydrogen, chlorine, bromine, methyl, ethyl, propyl or trifluoromethyl, Z very particularly preferably represents hydrogen, chlorine, bromine, methyl or represents the radical

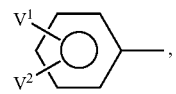

$V^1$ very particularly preferably represents hydrogen, fluorine, chlorine, methyl, ethyl, methoxy, trifluoromethyl or trifluoromethoxy, $V^2$ very particularly preferably represents hydrogen, fluorine, chlorine or methyl, CKE very particularly preferably represents one of the groups

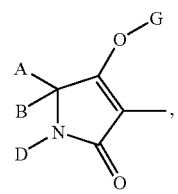
(1)

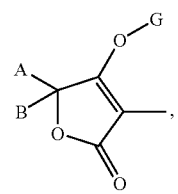
(2)

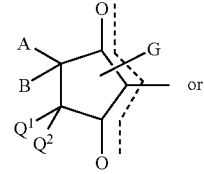
(5) or

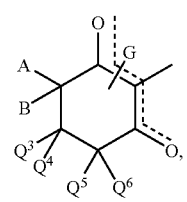
(6)

A very particularly preferably represents hydrogen, in each case optionally fluorine-substituted $C_1$-$C_4$-alkyl, $C_1$-$C_2$-alkoxy-$C_1$-$C_2$-alkyl or $C_3$-$C_6$-cycloalkyl, B very particularly preferably represents hydrogen or methyl, or A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, trifluoromethyl, methoxy, ethoxy, propoxy, butoxy or isobutoxy, or A, B and the carbon atom to which they are attached very particularly preferably represent $C_5$-$C_6$-cycloalkyl which is substituted by an alkylenedioxyl group which contains two not directly adjacent oxygen atoms and which, together with the carbon to which they are attached, form a further five- or six-membered ring, D very particularly preferably represents hydrogen, $C_1$-$C_4$-alkyl, $C_3$-$C_4$-alkenyl, $C_1$-$C_2$-alkoxy-$C_2$-$C_3$-alkyl or $C_3$-$C_6$-cycloalkyl, or A and D together very particularly preferably represent optionally substituted $C_3$-$C_5$-alkanediyl in which optionally one carbon atom is replaced by oxygen or sulphur, A and D (in the case of the compounds of the formula (I-1)) together with the atoms to which they are attached represent the group:

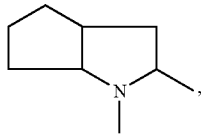

AD-1

A and $Q^1$ together very particularly preferably represent $C_3$-$C_4$-alkanediyl which is optionally mono- or disubstituted by methyl or methoxy, or $Q^1$ very particularly preferably represents hydrogen, $Q^2$ very particularly preferably represents hydrogen, $Q^4$, $Q^5$ and $Q^6$ independently of one another very particularly preferably represent hydrogen or methyl, $Q^3$ very particularly preferably represents hydrogen, methyl, ethyl or $C_3$-$C_6$-cycloalkyl, or $Q^3$ and $Q^4$ together with the carbon to which they are attached very particularly preferably represent a saturated $C_5$-$C_6$-ring which is optionally substituted by methyl or methoxy and in which optionally one ring member is replaced by oxygen, G very particularly preferably represents hydrogen (a) or represents one of the groups

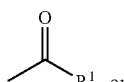

(b)

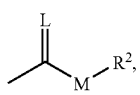

(c)

in which

E represents a metal ion equivalent or an ammonium ion,

L represents oxygen and

M represents oxygen or sulphur, $R^1$ very particularly preferably represents in each case optionally fluorine- or chlorine-substituted $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl or optionally fluorine-, chlorine-, methyl-, ethyl- or methoxy-substituted $C_3$-$C_6$-cycloalkyl, represents optionally fluorine-, chlorine-, bromine-, cyano-, nitro-, methyl-, methoxy-, trifluoromethyl- or trifluoromethoxy-substituted phenyl, $R^2$ very particularly preferably represents in each case optionally fluorine-substituted $C_1$-$C_{10}$-alkyl, $C_2$-$C_{10}$-alkenyl or $C_1$-$C_4$-alkoxy-$C_2$-$C_4$-alkyl or represents $C_3$-$C_6$-cycloalkyl, or represents in each case optionally fluorine-, chlorine-, cyano-, nitro-, methyl-, methoxy-, trifluoromethyl- or trifluoromethoxy-substituted phenyl or benzyl.

W especially preferably represents hydrogen, methyl, ethyl, chlorine or bromine, X especially preferably represents chlorine, bromine, methyl, ethyl or methoxy, Y especially preferably represents hydrogen, chlorine, bromine, methyl or ethyl, Z especially preferably represents hydrogen, chlorine, bromine, methyl, or represents the radical

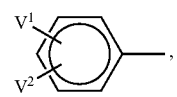

which is located in the para-position to the substituent X, $V^1$ especially preferably represents fluorine, chlorine, or trifluoromethyl, $V^2$ especially preferably represents hydrogen, fluorine or chlorine, CKE especially preferably represents one of the groups

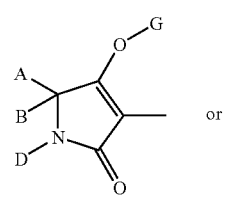

(1)

or

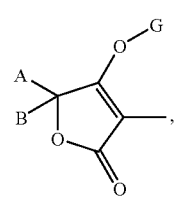

(2)

A, B and the carbon atom to which they are attached especially preferably represent unsaturated $C_5$-$C_6$-cycloalkyl in which optionally one ring member is replaced by oxygen and which is optionally monosubstituted by methyl, methoxy, ethoxy, propoxy or trifluoromethyl, D especially preferably represents hydrogen, G especially preferably represents hydrogen (a) or represents one of the groups

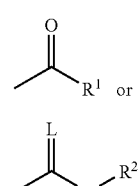

(b)

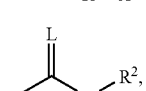

(c)

in which

L represents oxygen and

M represents oxygen or sulphur, $R^1$ especially preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or represents cyclopropyl or cyclohexyl, each of which is optionally monosubstituted by fluorine, chlorine, methyl or methoxy, represents phenyl which is optionally monosubstituted by fluorine, chlorine, bromine, cyano, nitro, methyl, methoxy, trifluoromethyl or trifluoromethoxy, $R^2$ especially preferably represents phenyl or benzyl, $C_1$-$C_8$-alkyl, $C_2$-$C_6$-alkenyl or $C_1$-$C_4$-alkoxy-$C_2$-$C_3$-alkyl, each of which is optionally mono- to trisubstituted by fluorine.

Emphasis is given to compounds of the formula (I) mentioned above in which the radicals are as defined below:

W especially represents hydrogen or methyl,

X especially represents chlorine, bromine, methyl or ethyl,

Y especially represents hydrogen, chlorine, bromine or methyl,

Z especially represents hydrogen, chlorine, bromine or methyl,

CKE especially represents the group

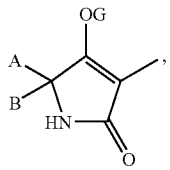

(1)

A, B and the carbon atom to which they are attached especially represent saturated $C_6$-cycloalkyl in which optionally one ring member is replaced by oxygen and which is optionally monosubstituted by methyl, trifluoromethyl, methoxy, ethoxy or propoxy, G especially represents hydrogen (a) or represents one of the groups

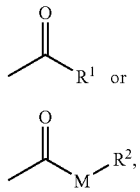

(b)

(c)

in which

M represents oxygen or sulphur, $R^1$ especially represents $C_1$-$C_6$-alkyl, $C_2$-$C_4$-alkenyl, methoxymethyl, ethoxymethyl, ethylthiomethyl, cyclopropyl, cyclopentyl, cyclohexyl or represents phenyl which is optionally monosubstituted by fluorine, chlorine, bromine, methyl, methoxy, trifluoromethyl, trifluoromethoxy, cyano or nitro, $R^2$ especially represents $C_1$-$C_6$-alkyl, $C_2$-$C_4$-alkenyl, methoxyethyl, ethoxyethyl, phenyl or benzyl, in the form of their isomer mixtures or pure isomers.

Particular emphasis, as examples, is given to compounds of the formula (I-1'), in which the radicals are as defined below:

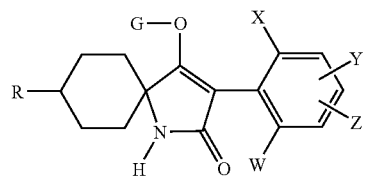

(I-1')

| Example No. | W | X | Y | Z | R | G | known from |
|---|---|---|---|---|---|---|---|
| I-1'-1 | $CH_3$ | $C_2H_5$ | 4-Br | H | $OCH_3$ | H | WO 97/02243; I-1-a-40, DE-A-04001433; Ia1 |
| I-1'-2 | H | Br | H | 5-$CH_3$ | $OCH_3$ | CO-i-$C_3H_7$ | WO 98/05638; I-1-b-33 |
| I-1'-3 | H | Br | H | 5-$CH_3$ | $OCH_3$ | $CO_2$—$C_2H_5$ | WO 98/05638; I-1-c-22 |
| I-1'-4 | H | $CH_3$ | H | 5-$CH_3$ | $OCH_3$ | H | WO 98/05638; I-1-a-4 WO 04/007448; I-a-1 |
| I-1'-5 | H | $CH_3$ | H | 5-$CH_3$ | $OCH_3$ | $CO_2$—$C_2H_5$ | WO 98/05638; I-1-c-4 WO 04/007448; I-c-1 |
| I-1'-6 | $CH_3$ | $CH_3$ | H | 3-Br | $OCH_3$ | H | WO 97/36868; I-1-a-17 |
| I-1'-7 | $CH_3$ | $CH_3$ | H | 3-Cl | $OCH_3$ | H | WO 97/36868; I-1-a-2 |
| I-1'-8 | H | Br | 4-$CH_3$ | 5-$CH_3$ | $OCH_3$ | CO-i-$C_3H_7$ | WO 97/01535; I-1-b-54 |
| I-1'-9 | H | $CH_3$ | 4-Cl | 5-$CH_3$ | $OCH_3$ | $CO_2$—$C_2H_5$ | WO 97/01535; I-1-c-18 |

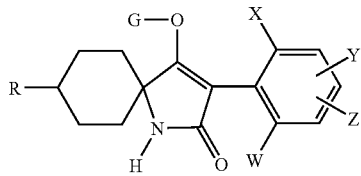
(I-1')

| Example No. | W | X | Y | Z | R | G | known from |
|---|---|---|---|---|---|---|---|
| I-1'-10 | CH₃ | CH₃ | 4-CH₃ | 3-CH₃ | OCH₃ | H | WO 97/36868; I-1-a-4 |
| I-1'-11 | CH₃ | CH₃ | H | 3-Br | OC₂H₅ | CO-i-C₃H₇ | WO 01/89300; I-10 |
| I-1'-12 | H | CH₃ | 4-CH₃ | 5-CH₃ | OC₂H₅ | CO-n-C₃H₇ | WO 97/01535; I-1-b-25 |
| I-1'-13 | H | CH₃ | 4-CH₃ | 5-CH₃ | OC₂H₅ | CO-i-C₃H₇ | WO 97/01535; I-1-b-22 |
| I-1'-14 | H | CH₃ | 4-CH₃ | 5-CH₃ | OC₂H₅ | CO-c-C₃H₅ | WO 97/01535; I-1-b-34 |

The general or preferred radical definitions or illustrations given above can be combined with one another as desired, i.e. including combinations between the respective ranges and preferred ranges.

Preference according to the invention is given to the use of the compounds of the formula (I) which contain a combination of the meanings given above as being preferred (preferable).

Particular preference according to the invention is given to the use of the compounds of the formula (I) which contain a combination of the meanings given above as being particularly preferred.

Very particular preference according to the invention is given to the use of the compounds of the formula (I) which contain a combination of the meanings given above as being very particularly preferred.

Especial preference according to the invention is given to the use of the compounds of the formula (I) which contain a combination of the meanings given above as being especially preferred.

Emphasis is given, according to the invention, to the use of the compounds of the formula (I) which contain a combination of the meanings given above as being especial.

Saturated or unsaturated hydrocarbon radicals such as alkyl or alkenyl can, as far as this is possible, in each case be straight-chain or branched, including in combination with heteroatoms, such as, for example, in alkoxy.

Unless indicated otherwise, optionally substituted radicals can be mono- or polysubstituted, where in the case of polysubstitution, the substituents can be identical or different.

In addition to the compounds mentioned in the examples, the following compounds of the formula (I-1-a) may be specifically mentioned:

TABLE 1

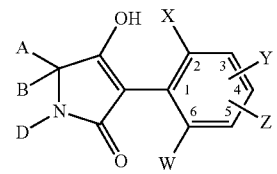

W = CH₃, X = CH₃, Y = 4-CH₃, Z = H.

| A | B | D |
|---|---|---|
| CH₃ | CH₃ | H |
| C₂H₅ | CH₃ | H |
| C₃H₇ | CH₃ | H |
| i-C₃H₇ | CH₃ | H |
| ▽ | CH₃ | H |
| —(CH₂)₄— | | H |
| —(CH₂)₅— | | H |
| —(CH₂)₂—O—(CH₂)₂— | | H |
| —CH₂—O—(CH₂)₃— | | H |
| —CH₂—CHCH₃—(CH₂)₃— | | H |
| —(CH₂)₂—CHCH₃—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—C(CH₃)₂—(CH₂)₂— | | H |

Table 2: A, B and D are as indicated in Table 1
 W=CH₃; X=CH₃; Y=4-Cl; Z=H.
Table 3: A, B and D are as indicated in Table 1
 W=CH₃; X=CH₃; Y=4-Br; Z=H.
Table 4: A, B and D are as indicated in Table 1
 W=C₂H₅; X=CH₃; Y=4-Cl; Z=H.
Table 5: A, B and D are as indicated in Table 1
 W=C₂H₅; X=CH₃; Y=4-Br; Z=H.
Table 6: A, B and D are as indicated in Table 1
 W=C₂H₅; X=C₂H₅; Y=4-Cl; Z=H.
Table 7: A, B and D are as indicated in Table 1
 W=C₂H₅; X=C₂H₅; Y=4-Br; Z=H.

Table 8: A, B and D are as indicated in Table 1
W=CH$_3$; X=Cl; Y=4-Cl; Z=H.
Table 9: A, B and D are as indicated in Table 1
W=CH$_3$; X=Br; Y=4-Br; Z=H.
Table 10: A, B and D are as indicated in Table 1
W=C$_1$H$_3$; X=Cl; Y=4-Br; Z=H
Table 11: A, B and D are as indicated in Table 1
W=CH$_3$; X=Br; Y=4-Cl; Z=H.
Table 12: A, B and D are as indicated in Table 1
W=C$_2$H$_5$; X=Cl; Y=4-Cl; Z=H.
Table 13: A, B and D are as indicated in Table 1
W=C$_2$H$_5$; X=Br; Y=4-Br; Z=H.
Table 14: A, B and D are as indicated in Table 1
W=C$_2$H$_5$; X=Cl; Y=4-Br; Z=H.
Table 15: A, B and D are as indicated in Table 1
W=C$_2$H$_5$; X=Br; Y=4-Cl; Z=H.
Table 16: A, B and D are as indicated in Table 1
W=H; X=Cl; Y=H; Z=H.
Table 17: A, B and D are as indicated in Table 1
W=H; X=Br; Y=H; Z=H.
Table 18: A, B and D are as indicated in Table 1
W=H; X=CH$_3$; Y=H; Z=H.
Table 19: A, B and D are as indicated in Table 1
W=H; X=CF$_3$; Y=H; Z=H.
Table 20: A, B and D are as indicated in Table 1
W=H; X=CH$_3$; Y=4-Cl; Z=H.
Table 21: A, B and D are as indicated in Table 1
W=H; X=Cl; Y=4-CH$_3$; Z=H.
Table 22: A, B and D are as indicated in Table 1
W=H; X=CH$_3$; Y=4-Br; Z=H.
Table 23: A, B and D are as indicated in Table 1
W=H; X=Br; Y=4-CH$_3$; Z=H.
Table 24: A, B and D are as indicated in Table 1
W=H; X=Cl; Y=4-Cl; Z=H.
Table 25: A, B and D are as indicated in Table 1
W=H; X=Cl; Y=4-Br; Z=H.
Table 26: A, B and D are as indicated in Table 1
W=H; X=Br; Y=4-Cl; Z=H.
Table 27: A, B and D are as indicated in Table 1
W=CH$_3$; X=Cl; Y=4-CH$_3$; Z=H.
Table 28: A, B and D are as indicated in Table 1
W=CH$_3$; X=Br; Y=4-CH$_3$; Z=H.
Table 29: A, B and D are as indicated in Table 1
W=C$_2$H$_5$; X=Cl; Y=4-CH$_3$; Z=H.
Table 30: A, B and D are as indicated in Table 1
W=C$_2$H$_5$; X=Br; Y=4-CH$_3$; Z=H.
Table 31: A, B and D are as indicated in Table 1
W=C$_2$H$_5$; X=CH$_3$; Y=4-CH$_3$; Z=H.
Table 32: A, B and D are as indicated in Table 1
W=C$_2$H$_5$; X=C$_2$H$_5$; Y=4-CH$_3$; Z=H.
Table 33: A, B and D are as indicated in Table 1
W=C$_2$H$_5$; X=C$_2$H$_5$; Y=4-C$_2$H$_5$; Z=H.
Table 34: A, B and D are as indicated in Table 1
W=H; X=CH$_3$; Y=4-CH$_3$; Z=5-CH$_3$.
Table 35: A, B and D are as indicated in Table 1
W=H; X=CH$_3$; Y=4-Cl; Z=5-CH$_3$.
Table 36: A, B and D are as indicated in Table 1
W=H; X=Br; Y=4-CH$_3$; Z=5-CH$_3$.
Table 37: A, B and D are as indicated in Table 1
W=H; X=Cl; Y=4-Cl; Z=5-CH$_3$.
Table 38: A, B and D are as indicated in Table 1
W=H; X=CH$_3$; Y=4-Br; Z=5-CH$_3$.
Table 39: A, B and D are as indicated in Table 1
W=H; X=Cl; Y=4-CH$_3$; Z=5-Cl.
Table 40: A, B and D are as indicated in Table 1
W=H; X=CH$_3$; Y=H; Z=5-CH$_3$.
Table 41: A, B and D are as indicated in Table 1
W=H; X=Cl; Y=H; Z=5-CH$_3$.
Table 42: A, B and D are as indicated in Table 1
W=H; X=Br; Y=H; Z=5-CH$_3$.
Table 43: A, B and D are as indicated in Table 1
W=CH$_3$; X=CH$_3$; Y=4-CH$_3$; Z=3-CH$_3$.
Table 44: A, B and D are as indicated in Table 1
W=CH$_3$; X=CH$_3$; Y=H; Z=3-Br.
Table 45: A, B and D are as indicated in Table 1
W=CH$_3$; X=CH$_3$; Y=4-CH$_3$; Z=3-Cl.
Table 46: A, B and D are as indicated in Table 1
W=CH$_3$; X=CH$_3$; Y=4-CH$_3$; Z=3-Br.
Table 47: A, B and D are as indicated in Table 1
W=CH$_3$; X=CH$_3$; Y=H; Z=3-Cl.

The compounds of the formula (I) are known in principle from the patent specifications mentioned at the outset, or they may be prepared according to the methods described therein.

Preferred meanings of the groups listed above in connection with the crop plant compatibility-improving compounds ("insecticide and acaricide safeners") of the formulae (IIa), (IIb), (IIc), (IId) and (IIe) are defined below.

m preferably represents the number 0, 1, 2, 3 or 4, $A^1$ preferably represents one of the divalent heterocyclic groupings shown below n preferably represents the number 0, 1, 2, 3 or 4, $A^2$ preferably represents in each case optionally methyl-, ethyl-, methoxycarbonyl-, ethoxycarbonyl- or allyloxycarbonyl-substituted methylene or ethylene, $R^8$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^9$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^{10}$ preferably represents in each case optionally fluorine-, chlorine- and/or bromine-substituted methyl, ethyl, n- or i-propyl, $R^{11}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, $R^{12}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, turyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^{11}$ represents one of the radicals —$CH_2$—O—$CH_2$—$CH_2$— and —$CH_2$—$CH_2$—O—$CH_2$—$CH_2$—, which are optionally substituted by methyl, ethyl, furyl, phenyl, a fused-on benzene ring or by two substituents which together with the C atom to which they are attached form a 5- or 6-membered carbocycle, $R^{13}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl, $R^{14}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl, $R^{15}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl, $X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, t preferably represents the number 0, 1, 2, 3 or 4, v preferably represents the number 0, 1, 2, 3 or 4, $R^{16}$ preferably represents hydrogen, methyl, ethyl, n- or i-propyl, $R^{17}$ preferably represents hydrogen, methyl, ethyl, n- or i-propyl, $R^{18}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, $R^{19}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl, $R^{20}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{19}$ represents in each case optionally methyl- or ethyl-substituted butane-1,4-diyl(trimethylene), pentane-1,5-diyl, 1-oxa-butane-1,4-diyl or 3-oxa-pentane-1,5-diyl, $X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, $X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, Examples of compounds of the formula (IIa) which are very particularly preferred as insecticide and acaricide safeners according to the invention are listed in the table below.

Table Examples of the compounds of the formula (IIa)

| Example No. | (Positions) $(X^1)_m$ | $A^1$ | $R^8$ |
|---|---|---|---|
| IIa-1 | (2) Cl, (4) Cl | (pyrazoline with N-methyl, C-methyl, and C(=O)OCH₃ substituent) | $OCH_3$ |
| IIa-2 | (2) Cl, (4) Cl | (pyrazoline with N-methyl, C-methyl, and C(=O)OC₂H₅ substituent) | $OCH_3$ |
| IIa-3 | (2) Cl, (4) Cl | (pyrazoline with N-methyl, C-methyl, and C(=O)OCH₃ substituent) | $OC_2H_5$ |

-continued (IIa)

| Example No. | (Positions) (X¹)ₘ | A¹ | R⁸ |
|---|---|---|---|
| IIa-4 | (2) Cl, (4) Cl | 1-methyl-3-methyl-5-(ethoxycarbonyl,methyl)-4,5-dihydropyrazol-5-yl | OC$_2$H$_5$ |
| IIa-5 | (2) Cl | 1-methyl-3-methyl-5-phenylpyrazol-5-yl | OCH$_3$ |
| IIa-6 | (2) Cl, (4) Cl | 1-methyl-3-methyl-5-phenylpyrazol-5-yl | OCH$_3$ |
| IIa-7 | (2) F | 1-methyl-3-methyl-5-phenylpyrazol-5-yl | OCH$_3$ |
| IIa-8 | (2) F | 1-methyl-3-methyl-5-(2-chlorophenyl)pyrazol-5-yl | OCH$_3$ |
| IIa-9 | (2) Cl, (4) Cl | 1-methyl-3-methyl-5-trichloromethyl-1,2,4-triazol-5-yl | OC$_2$H$_5$ |
| IIa-10 | (2) Cl, (4) CF$_3$ | 1-methyl-3-methyl-5-phenyl-1,2,4-triazol-5-yl | OCH$_3$ |
| IIa-11 | (2) Cl | 1-methyl-3-methyl-5-(2-fluorophenyl)pyrazol-5-yl | OCH$_3$ |
| IIa-12 | — | 3-methyl-5-methyl-5-phenyl-4,5-dihydroisoxazol-5-yl | OC$_2$H$_5$ |
| IIa-13 | (2) Cl, (4) Cl | 1-methyl-3-methyl-5-methylpyrazol-5-yl | OC$_2$H$_5$ |
| IIa-14 | (2) Cl, (4) Cl | 1-methyl-3-methyl-5-isopropylpyrazol-5-yl | OC$_2$H$_5$ |
| IIa-15 | (2) Cl, (4) Cl | 1-methyl-3-methyl-5-tert-butylpyrazol-5-yl | OC$_2$H$_5$ |
| IIa-16 | (2) Cl, (4) Cl | 3-methyl-5-ethyl-4,5-dihydroisoxazol-5-yl | OC$_2$H$_5$ |
| IIa-17 | (2) Cl, (4) Cl | 3-methyl-5-methyl-4,5-dihydroisoxazol-5-yl | OC$_2$H$_5$ |
| IIa-18 | — | 3-methyl-5-methyl-5-phenyl-4,5-dihydroisoxazol-5-yl | OH |

Examples of compounds of the formula (IIb) which are very particularly preferred as insecticide and acaricide safeners according to the invention are listed in the table below.

TABLE

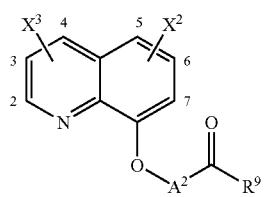

(IIb)

Examples of the compounds of the formula (IIb)

| Example No. | (Position) $X^2$ | (Position) $X^3$ | $A^2$ | $R^9$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | (complex structure with CH_2=CH-CH_2-O-CH_2-CH(O-)-CH_3) |
| IIb-13 | (5) Cl | — | $CH_2OCH_2CH=CH_2$ on a CH branch | (ester of isobutyric acid) |
| IIb-14 | (5) Cl | — | $C_2H_5$ on CH (ester) | $OC_2H_5$ |
| IIb-15 | (5) Cl | — | $CH_3$ on CH (ester) | $OCH_3$ |

Examples of the compounds of the formula (IIc) which are very particularly preferred as insecticide and acaricide safeners according to the invention are listed in the table below.

TABLE

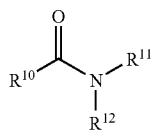

(IIc)

Examples of the compounds of the formula (IIc)

| Example No. | $R^{10}$ | $N(R^{11}, R^{12})$ |
|---|---|---|
| IIc-1 | $CHCl_2$ | $N(CH_2CH=CH_2)_2$ |
| IIc-2 | $CHCl_2$ | 2,2-dimethyl-oxazolidin-3-yl (N-methyl) |
| IIc-3 | $CHCl_2$ | 2,2-dimethyl-5-methyl-oxazolidin-3-yl |
| IIc-4 | $CHCl_2$ | 1-oxa-4-azaspiro[4.5]decan-4-yl |
| IIc-5 | $CHCl_2$ | 2,2-dimethyl-5-phenyl-oxazolidin-3-yl |
| IIc-6 | $CHCl_2$ | 3-methyl-2,3-dihydro-4H-1,4-benzoxazin-4-yl |
| IIc-7 | $CHCl_2$ | 2,2-dimethyl-5-(furan-2-yl)-oxazolidin-3-yl |

Examples of the compounds of the formula (IId) which are very particularly preferred as insecticide and acaricide safeners according to the invention are listed in the table below.

TABLE

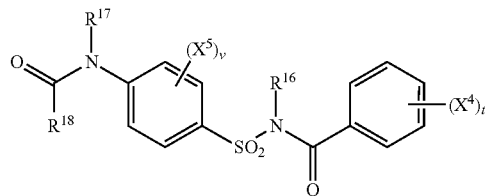

(IId)

Examples of the compounds of the formula (IId)

| Example No. | R¹⁶ | R¹⁷ | R¹⁸ | (Positions) (X⁴)_t | (Positions) (X⁵)_v |
|---|---|---|---|---|---|
| IId-1 | H | H | CH₃ | (2) OCH₃ | — |
| IId-2 | H | H | C₂H₅ | (2) OCH₃ | — |
| IId-3 | H | H | C₃H₇-n | (2) OCH₃ | — |
| IId-4 | H | H | C₃H₇-i | (2) OCH₃ | — |
| IId-5 | H | H | cyclopropyl | (2) OCH₃ | — |
| IId-6 | H | H | CH₃ | (2) OCH₃ (5) CH₃ | — |
| IId-7 | H | H | C₂H₅ | (2) OCH₃ (5) CH₃ | — |
| IId-8 | H | H | C₃H₇-n | (2) OCH₃ (5) CH₃ | — |
| IId-9 | H | H | C₃H₇-i | (2) OCH₃ (5) CH₃ | — |
| IId-10 | H | H | cyclopropyl | (2) OCH₃ (5) CH₃ | — |
| IId-11 | H | H | OCH₃ | (2) OCH₃ (5) CH₃ | — |
| IId-12 | H | H | OC₂H₅ | (2) OCH₃ (5) CH₃ | — |
| IId-13 | H | H | OC₃H₇-i | (2) OCH₃ (5) CH₃ | — |
| IId-14 | H | H | SCH₃ | (2) OCH₃ (5) CH₃ | — |
| IId-15 | H | H | SC₂H₅ | (2) OCH₃ (5) CH₃ | — |
| IId-16 | H | H | SC₃H₇-i | (2) OCH₃ (5) CH₃ | — |
| IId-17 | H | H | NHCH₃ | (2) OCH₃ (5) CH₃ | — |
| IId-18 | H | H | NHC₂H₅ | (2) OCH₃ (5) CH₃ | — |
| IId-19 | H | H | NHC₃H₇-i | (2) OCH₃ (5) CH₃ | — |
| IId-20 | H | H | NH-cyclopropyl | (2) OCH₃ (5) CH₃ | — |
| IId-21 | H | H | NHCH₃ | (2) OCH₃ | — |
| IId-22 | H | H | NHC₃H₇-i | (2) OCH₃ | — |
| IId-23 | H | H | N(CH₃)₂ | (2) OCH₃ | — |
| IId-24 | H | H | N(CH₃)₂ | (3) CH₃ (4) CH₃ | — |
| IId-25 | H | H | CH₂—O—CH₃ | (2) OCH₃ | — |

Examples of the compounds of the formula (IIe) which are very particularly preferred as insecticide and acaricide safeners according to the invention are listed in the table below.

TABLE

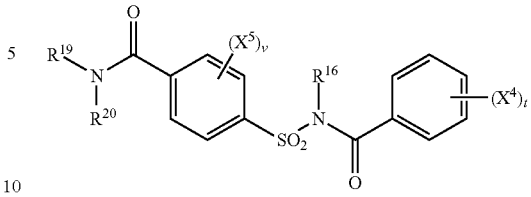

(IIe)

Examples of the compounds of the formula (IIe)

| Example No. | R¹⁶ | R¹⁹ | R²⁰ | (Positions) (X⁴)_t | (Positions) (X⁵)_v |
|---|---|---|---|---|---|
| IIe-1 | H | H | CH₃ | (2) OCH₃ | — |
| IIe-2 | H | H | C₂H₅ | (2) OCH₃ | — |
| IIe-3 | H | H | C₃H₇-n | (2) OCH₃ | — |
| IIe-4 | H | H | C₃H₇-i | (2) OCH₃ | — |
| IIe-5 | H | H | cyclopropyl | (2) OCH₃ | — |
| IIe-6 | H | CH₃ | CH₃ | (2) OCH₃ | — |
| IIe-7 | H | H | CH₃ | (2) OCH₃ (5) CH₃ | — |
| IIe-8 | H | H | C₂H₅ | (2) OCH₃ (5) CH₃ | — |
| IIe-9 | H | H | C₃H₇-n | (2) OCH₃ (5) CH₃ | — |
| IIe-10 | H | H | C₃H₇-i | (2) OCH₃ (5) CH₃ | — |
| IIe-11 | H | H | cyclopropyl | (2) OCH₃ (5) CH₃ | — |
| IIe-12 | H | CH₃ | CH₃ | (2) OCH₃ (5) CH₃ | — |

Most preferred compounds which improve crop plant compatibility [component (b)] are cloquintocet-mexyl, fenchlorazol-ethyl, isoxadifen-ethyl, mefenpyr-diethyl, firilazole, fenclorim, cumyluron, dymron, dichlormid, dimepiperate and the compounds IIe-5 and IIe-11 and particular emphasis is given to cloquintocet-mexyl, isoxadifen-ethyl, mefenpyr-diethyl, furilazole, dichlormid, fenclorim and IIe-5.

Examples of the selectively insecticidal and/or acaricidal 1 combinations according to the invention of in each case one active compound of the formula (I) and in each case one of the safeners defined above are listed in the table below.

Table Examples of the combinations according to the invention

| Active compound of the formula (I) | Safener |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-1 | dichlormid |
| I-2 | cloquintocet-mexyl |

-continued

| Active compound of the formula (I) | Safener |
|---|---|
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-2 | IIe-5 |
| I-2 | dichlormid |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-3 | dichlormid |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-4 | dichlormid |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-5 | dichlormid |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-6 | dichlormid |

The compounds of the general formula (IIa) to be used as safeners are known and/or can be prepared by processes known per se (cf. WO-A-91/07874, WO-A-95/07897).

The compounds of the general formula (IIb) to be used as safeners are known and/or can be prepared by processes known per se (cf. EP-A-191736).

The compounds of the general formula (IIc) to be used as safeners are known and/or can be prepared by processes known per se (cf. DE-A-2218097, DE-A-2350547).

The compounds of the general formula (IId) to be used as safeners are known and/or can be prepared by processes known per se (cf. DE-A-19621522/U.S. Pat. No. 6,235,680).

The compounds of the general formula (IIe) to be used as safeners are known and/or can be prepared by processes known per se (cf. WO-A-99/66795/U.S. Pat. No. 6,251,827).

Surprisingly, it has now been found that the above-defined active compound combinations of substituted ketoenols of the general formula (I) and safeners (antidotes) of group (b) listed above, whilst being tolerated very well by useful plants, have good insecticidal and/or acaricidal activity and can be used in various crops, in particular in cereals (especially wheat and barley), but also in millet, maize and rice, for the selective control of insects.

Here, it has to be considered to be surprising that, from a large number of known safeners or antidotes which are capable of antagonizing the damaging effect of a herbicide on the crop plants, it is in particular the abovementioned compounds of group (b) which are suitable for neutralizing the damaging effect of substituted cyclic ketoenols of the formula (I) on the crop plants virtually completely without negatively affecting the insecticidal and/or acaricidal activity.

Furthermore, it has to be considered to be completely surprising that compounds from group (b) listed above are not only capable of virtually completely neutralizing the damaging effect of substituted cyclic ketoenols of the formula (I) on the crop plants but in some cases even enhance the insecticidal and/or acaricidal activity of the substituted cyclic ketoenols of the formula (I), so that a synergistic effect can be observed.

Emphasis is given here to the particularly advantageous effect of the particularly and most preferred combination partners from group (b), in particular in respect of sparing cereal plants, such as, for example, wheat, barley and rye, but also millet, maize and rice, as crop plants.

The combinations of active compounds can be used, for example, for the following plants:

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.*

Monocotyledonous crops of the genera: *Oryza, Zea, Triticum, Hordeum, Avena, Secale, Sorghum, Panicum, Saccharum, Ananas, Asparagus, Allium.*

However, the use of the combinations of active compounds is by no means limited to these genera but equally also extends to other plants.

The advantageous effect of the combinations of active compounds is particularly strongly pronounced at certain concentration ratios. However, the weight ratios of the active compounds in the combinations of active compounds can be varied within relatively wide ranges. In general, 0.001 to 1000 parts by weight, preferably 0.01 to 100 parts by weight, particularly preferably 0.05 to 10 parts by weight and most preferably 0.07 to 1.5 parts by weight of one of the crop plant compatibility-improving compounds (antidotes/safeners) mentioned above under (b) are present per part by weight of active compound of the formula (I) or salts thereof.

The active compounds or active compound combinations can be converted into the customary formulations, such as solutions, emulsions, wettable powders, suspensions, powders, dusts, pastes, soluble powders, granules, suspoemulsion concentrates, natural and synthetic materials impregnated with active compound and microencapsulations in polymeric materials.

These formulations are produced in a known manner, for example by mixing the active compounds with extenders, that is, liquid solvents and/or solid carriers, optionally with the use of surface-active agents, that is, emulsifiers and/or dispersants and/or foam formers.

If the extender used is water, it is also possible to use for example organic solvents as auxiliary solvents. Suitable liquid solvents are mainly: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters thereof, ketones, such as acetone, methyl ethyl ketone, methyl isobutyl ketone or cyclohexanone, strongly polar solvents, such as dimethylformamide and dimethyl sulphoxide, and water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable as solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable as emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable as dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active compounds, including the active compounds with a safening effect, preferably between 0.5 and 90%.

The combinations of active compounds are generally applied in the form of ready-to-use formulations. However, the active compounds contained in the combinations of active compounds may also be applied in the form of individual formulations which are mixed upon use, that is, in the form of tank mixes.

The combinations of active compounds, as such or in their formulations, may furthermore also be used as a mixture with other known herbicides, again with ready-to-use formulations or tank mixes being possible. A mixture with other known active compounds, such as fungicides, insecticides, acaricides, nematicides, attractants, sterilants, bactericides, bird repellents, growth substances, plant nutrients and soil conditioners is also possible. It may furthermore be advantageous for specific applications, in particular for the post-emergence method, to incorporate into the formulations plant-compatible mineral or vegetable oils (for example the commercial product "Rako Binol") or ammonium salts, such as, for example, ammonium sulphate or ammonium thiocyanate, as further additives.

The combinations of active compounds can be used as such, in the form of their formulations or the use forms which are prepared from these formulations by further dilution, such as ready-to-use solutions, suspensions, emulsions, powders, pastes and granules. Application is effected in the customary manner, for example by watering, spraying, atomizing, dusting or broadcasting.

The application rates of the combinations of active compound can be varied within a certain range; they depend inter alia on the weather and on the soil factors. In general, the application rates are between 0.005 and 5 kg per ha, preferably between 0.01 and 2 kg per ha, particularly preferably between 0.05 and 1.0 kg per ha.

The combinations of active compounds can be applied before and after emergence of the plants, i.e. by the pre-emergence and the post-emergence method.

Depending on their properties, the safeners to be used can be employed for pretreating the seed of the crop plant (seed dressing) or be incorporated into the seed furrows before sowing or, together with the herbicide, be applied before or after emergence of the plants.

The combinations of active compounds are suitable for controlling animal pests, preferably arthropods and nematodes, in particular insects and arachnids, encountered in agriculture, in animal healthcare, in forests, in the protection of stored products and in the protection of materials, and also in the hygiene sector. They are effective against normally sensitive and resistant species and against all or individual stages of development. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps,*

*Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the arachnids, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

When used as insecticides, the combinations of active compounds can furthermore be present, in their commercial formulations and in the use forms prepared from these formulations, as a mixture with synergists. Synergists are compounds which enhance the activity of the active compounds, without it being necessary for the added synergist to be active for its part.

The content of active compounds of the use forms prepared from the commercial formulations may vary within wide ranges. The concentration of active compounds of the use forms may be from 0.0000001 to 95% by weight of active compound and is preferably from 0.0001 to 1% by weight.

Application is carried out in a customary manner adapted to the use forms.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeder's certificates. Parts of plants are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant varieties, or those obtained by conventional biological breeding methods, such as crossing or protoplast fusion, and parts thereof, are treated. In a further preferred embodiment, transgenic plants and plant varieties obtained by genetic engineering methods, if appropriate in combination with conventional methods (Genetically Modified Organisms), and parts thereof are treated. The term "parts" or "parts of plants" or "plant parts" has been explained above.

Particularly preferably, plants of the plant varieties which are in each case commercially available or in use are treated according to the invention.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya bean), Knock-Out® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant varieties having these or still-to-be-developed genetic traits, which plant varieties will be developed and/or marketed in the future.

The plants listed can be treated according to the invention in a particularly advantageous manner with the active compound mixtures. The preferred ranges stated above for the mixtures also apply to the treatment of these plants. Particular emphasis is given to the treatment of plants with the mixtures specifically mentioned in the present text.

USE EXAMPLES

Method: Safener test after spraying
Solvent: 7 parts by weight of DMF
Emulsifier: 2 parts by weight of alkylaryl polyglycol ether To produce a suitable preparation of active compound, 1 part by weight of active compound is mixed with the stated amounts of solvent and emulsifier, and the concentrate is diluted with tap water to the desired concentration. The desired amount of safener (in the case of mefenpyr-diethyl as WP 20) is mixed into the water used for dilution. Furthermore, 2 g of a.i./l of rapeseed oil methyl ester 500 EW are added. Leaves of winter barley at the 2-leaf stage which are infested by the bird cherry-oat aphid (*Rhopalosiphum padi*) are treated with the desired active compound and safener concentrations using a spray boom, the water application rate being 300 l/ha. Per variant, the test is carried out at least twice. Evaluation is carried out after 7 d and/or 14 d by assessing the plant damage in % and the kill of the grain aphids in % compared to the untreated control. 100% damage means that the plant has died, and 0% means no damage. 100% effect on the grain aphids means that all aphids have been killed; 0% means that none of the aphids have been killed.

Results for greenhouse trials with safener after spraying against *Rhopalosiphum padi* on summer barley/winter barley

TABLE

|  | Application rate | Kill (%) | Damage (%) | |
|---|---|---|---|---|
|  | g of a.i./ha | 7 d | 7 d | 14 d |
| Example I-1'-1 | 40 | 70 | 80 | 90 |
| Example I-1'-1 + mefenpyr-diethyl | 40 + 100 | 97 | 50 | 40 |
| mefenpyr-diethyl | 100 | 0 | 0 | 0 |

TABLE

|  | Application rate | Kill (%) | Damage to new growth (%) | |
|---|---|---|---|---|
|  | g of a.i./ha | 7 d | 7 d | 14 d |
| Example I-1'-1 | 40 | 70 | 100 | 100 |
| Example I-1'-1 + mefenpyr-diethyl | 40 + 100 | 97 | 30 | 0 |
| mefenpyr-diethyl | 100 | 0 | 0 | 0 |

Formula to Calculate the Kill Rate of a Combination of Two Active Compounds

The expected activity of a given combination of two active compounds can be calculated as follows (cf. Colby, S. R., "Calculating Synergistic and Antagonistic Responses of Herbicide Combinations", Weeds 15, pages 20-22, 1967):

if

X is the kill rate expressed in % of the untreated control when employing active compound A at an application rate of m ppm, Y is the kill rate expressed in % of the untreated control when employing active compound B at an application rate of n ppm, E is the kill rate expressed in % of the untreated control when using the active compounds A and B at application rates of m and n ppm, $$\text{then } E = X + Y - \frac{X \times Y}{100}$$

If the actual insecticidal kill rate exceeds the calculated value, the kill of the combination is superadditive, i.e. a synergistic effect is present. In this case, the actually observed kill rate must exceed the value calculated using the above formula for the expected kill rate (E).

Examples of Spray Application

Solvent: water
Adjuvant: rapeseed oil methyl ester (0.1% of a.i./l)

To prepare a suitable application solution, 1 part by weight of formulation is mixed with the appropriate amount of water and the adjuvant and the concentrate is diluted with water to the desired concentration.

Example A

Aphis gossypii Test

Cotton plants (*Gossypium herbaceum*) which are heavily infested by the cotton aphid (*Aphis gossypii*) are sprayed to runoff point with the desired concentration of the application solution.

Example B

Metopolophium dirhodum Test

Barley plants (*Hordeum vulgare*) which are heavily infested by a grain aphid (*Metopolophium dirhodum*) are sprayed to runoff point with the desired concentration of the application solution.

Example C

Myzus persicae Test

Bell pepper plants (*Capsicum sativum*) which are heavily infested by the green peach aphid (*Myzus persicae*) are sprayed to runoff point with the desired concentration of the application solution.

After the desired period of time, the kill in % is determined. 100% means that all aphids have been killed; 0% means that none of the aphids have been killed. The determined kill rates are entered in Colby's formula.

In this test, for example, the following active compound combination in accordance with the present application shows a synergistically enhanced activity compared to the active compounds applied individually:

TABLE A

Plant-damaging insects
*Aphis gossypii* - Test

| Formulation | Concentration in ppm | Kill rate in % after $7^d$ found* | calc.** |
|---|---|---|---|
| Ex. (I-1'-5) SC 240 | 20 | 30 | |
| Isoxadifen-ethyl WG 50 | 50 | 0 | |
| Ex. (I-1'-5) + Isoxadifen-ethyl (1:2.5) according to the invention | 20 + 50 | 50 | 30 |
| Mefenpyr-diethyl WG 15 | 100 | 0 | |
| Ex. (I-1'-5) + Mefenpyr-diethyl (1:5) according to the invention | 20 + 100 | 55 | 30 |
| Ex. (IIe-5) a.i. | 100 | 0 | |
| Ex. (I-1'-5) + (Ex. IIe-5) according to the invention | 20 + 100 | 50 | 30 |
| Cloquintocet-mexyl WP 20 | 100 | 5 | |
| Ex. (I-1'-5) + Cloquintocet-mexyl (1:5) according to the invention | 20 + 100 | 70 | 33.5 |
| Dichlormid a.i. | 100 | 0 | |
| Ex. (I-1'-5) + Dichlormid (1:5) according to the invention | 20 + 100 | 55 | 30 |

*found = activity found
**calc. = activity calculated using Colby's formula

TABLE B

Plant-damaging insects
*Metopolophium dirhodum*-Test

| Formulation | Concentration in ppm | Kill rate in % after $7^d$ found* | calc.** |
|---|---|---|---|
| Ex. (I-1'-5) SC 240 | 20 | 15 | |
| Isoxadifen-ethyl WG 50 | 25 | 0 | |
| Ex. (I-1'-5) + Isoxadifen-ethyl (1:1.25) according to the invention | 20 + 25 | 35 | 15 |
| Ex. (IIe-5) | 100 | 0 | |
| Ex. (I-1'-5) + (Ex. IIe-5) (1:5) according to the invention | 20 + 100 | 35 | 15 |
| Dichloramid a.i. | 100 | 0 | |
| Ex. (I-1'-5) + Dichloramid(1:5) according to the invention | 20 + 100 | 40 | 15 |
| Fenclorim a.i. | 25 | 0 | |
| Ex. (I-1'-5) + Fenclorim (1:1.25) according to the invention | 20 + 25 | 35 | 15 |

*found = activity found
**calc. = activity calculated using Colby's formula

TABLE C

Plant-damaging insects
*Myzus persicae* - Test

| Formulation | Concentration in ppm | Kill rate in % after $7^d$ found* | calc.** |
|---|---|---|---|
| Ex. (I-1'-5) SC 240 | 20 | 0 | |
| Mefenpyr-diethyl WG 15 | 100 | 5 | |
| Ex. (I-1'-5) + Mefenpyr-diethyl (1:5) according to the invention | 20 + 100 | 35 | 5 |
| Ex. (IIe-5) | 100 | 5 | |
| Ex. (I-1'-5) + (Ex. IIe-5) (1:5) according to the invention | 20 + 100 | 70 | 5 |
| Cloquintocet-mexyl WP 20 | 25 | 0 | |
| Ex. (I-1'-5) + Cloquintocet-mexyl (1:1.25) according to the invention | 20 + 25 | 80 | 0 |
| Dichlormid a.i. | 100 | 0 | |
| Ex. (I-1'-5) + Dichlormid (1:5) according to the invention | 20 + 100 | 94 | 0 |
| Fenclorim a.i. | 50 | 0 | |
| Ex. (I-1'-5) + Fenclorim (1:2.5) according to the invention | 20 + 50 | 90 | 0 |

55

TABLE C-continued

Plant-damaging insects
*Myzus persicae* - Test

| Formulation | Concentration in ppm | Kill rate in % after 7$^d$ found* | calc.** |
|---|---|---|---|
| Furilazole a.i. | 50 | 0 | |
| Ex. (I-1'-5) + Furilazole (1:2.5) according to the invention | 20 + 50 | 87.5 | 0 |

*found = activity found
**calc. = activity calculated using Colby's formula

The invention claimed is:

1. A method for controlling insects or arachnids comprising contacting said insects or arachnids on a crop plant with a composition which comprises synergistically effective amounts of a compound of the formula (I-1'),

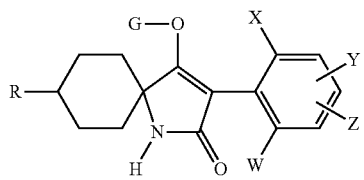
(I-1')

in which the radicals are as defined below:

| W | X | Y | Z | R | G |
|---|---|---|---|---|---|
| CH$_3$ | C$_2$H$_5$ | 4-Br | H | OCH$_3$ | H |
| H | Br | H | 5-CH$_3$ | OCH$_3$ | CO-i-C$_3$H$_7$ |
| H | Br | H | 5-CH$_3$ | OCH$_3$ | CO$_2$—C$_2$H$_5$ |
| H | CH$_3$ | H | 5-CH$_3$ | OCH$_3$ | H |
| H | CH$_3$ | H | 5-CH$_3$ | OCH$_3$ | CO$_2$—C$_2$H$_5$ |
| CH$_3$ | CH$_3$ | H | 3-Br | OCH$_3$ | H |
| CH$_3$ | CH$_3$ | H | 3-Cl | OCH$_3$ | H |
| H | Br | 4-CH$_3$ | 5-CH$_3$ | OCH$_3$ | CO-i-C$_3$H$_7$ |
| H | CH$_3$ | 4-Cl | 5-CH$_3$ | OCH$_3$ | CO$_2$—C$_2$H$_5$ |
| CH$_3$ | CH$_3$ | 4-CH$_3$ | 3-CH$_3$ | OCH$_3$ | H |
| CH$_3$ | CH$_3$ | H | 3-Br | OC$_2$H$_5$ | CO-i-C$_3$H$_7$ |
| H | CH$_3$ | 4-CH$_3$ | 5-CH$_3$ | OC$_2$H$_5$ | CO-n-C$_3$H$_7$ |
| H | CH$_3$ | 4-CH$_3$ | 5-CH$_3$ | OC$_2$H$_5$ | CO-i-C$_3$H$_7$ |
| H | CH$_3$ | 4-CH$_3$ | 5-CH$_3$ | OC$_2$H$_5$ | CO-c-C$_3$H$_5$ | and a crop plant compatibility-improving compound selected from the group consisting of cloquintocet-mexyl, isoxadifen-ethyl, mefenpyr-diethyl, dichlormid, furilazole, fenclorim and the compound

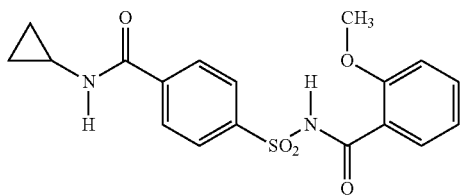

wherein the crop plant is in need of protection from said insects or arachnids.

2. A composition comprising a synergistically effective amount of compounds comprising

56

(a) at least one compound of the formula (I-1')

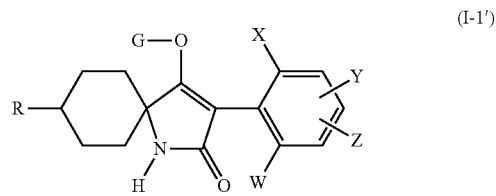
(I-1')

in which the substituents W, X, Y, Z, R and G are defined below

| W | X | Y | Z | R | G |
|---|---|---|---|---|---|
| H | Br | H | 5-CH$_3$ | OCH$_3$ | CO-i-C$_3$H$_7$ |
| H | Br | H | 5-CH$_3$ | OCH$_3$ | CO$_2$—C$_2$H$_5$ |
| H | CH$_3$ | H | 5-CH$_3$ | OCH$_3$ | H |
| H | CH$_3$ | H | 5-CH$_3$ | OCH$_3$ | CO$_2$—C$_2$H$_5$ |
| CH$_3$ | CH$_3$ | H | 3-Br | OCH$_3$ | H |
| CH$_3$ | CH$_3$ | H | 3-Cl | OCH$_3$ | H |
| H | Br | 4-CH$_3$ | 5-CH$_3$ | OCH$_3$ | CO-i-C$_3$H$_7$ |
| H | CH$_3$ | 4-Cl | 5-CH$_3$ | OCH$_3$ | CO$_2$—C$_2$H$_5$ |
| CH$_3$ | CH$_3$ | 4-CH$_3$ | 3-CH$_3$ | OCH$_3$ | H |
| CH$_3$ | CH$_3$ | H | 3-Br | OC$_2$H$_5$ | CO-i-C$_3$H$_7$ |
| H | CH$_3$ | 4-CH$_3$ | 5-CH$_3$ | OC$_2$H$_5$ | CO-n-C$_3$H$_7$ |
| H | CH$_3$ | 4-CH$_3$ | 5-CH$_3$ | OC$_2$H$_5$ | CO-i-C$_3$H$_7$ |
| H | CH$_3$ | 4-CH$_3$ | 5-CH$_3$ | OC$_2$H$_5$ | CO-c-C$_3$H$_5$ | and (b) at least one crop plant compatibility-improving compound selected from the group consisting of cloquintocet-mexyl, isoxadifen-ethyl, mefenpyr-diethyl, dichlormid, furilazole, fenclorim and the compound

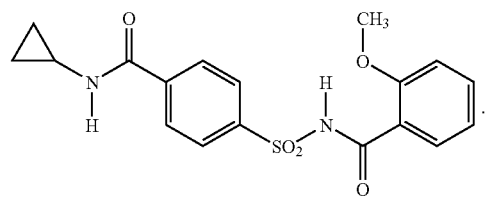

3. A composition according to claim 2, which comprises the compound wherein W is H, X is CH$_3$, Y is H, Z is 5-CH$_3$, R is OCH$_3$ and G is CO$_2$—C$_2$H$_5$ (I-1'-5).

4. The method according to claim 1 wherein the compound of formula (I-1') is a compound in which the radicals are as defined below:

| W | X | Y | Z | R | G |
|---|---|---|---|---|---|
| H | Br | H | 5-CH$_3$ | OCH$_3$ | CO-i-C$_3$H$_7$ |
| H | Br | H | 5-CH$_3$ | OCH$_3$ | CO$_2$—C$_2$H$_5$ |
| H | CH$_3$ | H | 5-CH$_3$ | OCH$_3$ | H |
| H | CH$_3$ | H | 5-CH$_3$ | OCH$_3$ | CO$_2$—C$_2$H$_5$ |
| CH$_3$ | CH$_3$ | H | 3-Br | OCH$_3$ | H |
| CH$_3$ | CH$_3$ | H | 3-Cl | OCH$_3$ | H |
| H | Br | 4-CH$_3$ | 5-CH$_3$ | OCH$_3$ | CO-i-C$_3$H$_7$ |
| H | CH$_3$ | 4-Cl | 5-CH$_3$ | OCH$_3$ | CO$_2$—C$_2$H$_5$ |
| CH$_3$ | CH$_3$ | 4-CH$_3$ | 3-CH$_3$ | OCH$_3$ | H |
| CH$_3$ | CH$_3$ | H | 3-Br | OC$_2$H$_5$ | CO-i-C$_3$H$_7$ |
| H | CH$_3$ | 4-CH$_3$ | 5-CH$_3$ | OC$_2$H$_5$ | CO-n-C$_3$H$_7$ |

-continued

| W | X | Y | Z | R | G |
|---|---|---|---|---|---|
| H | CH₃ | 4-CH₃ | 5-CH₃ | OC₂H₅ | CO-i-C₃H₇ |
| H | CH₃ | 4-CH₃ | 5-CH₃ | OC₂H₅ | CO-c-C₃H₅. |

5. The method according to claim 4 wherein the compound of formula (I-1') is the compound wherein W is H, X is CH₃, Y is H, Z is 5-CH₃, R is OCH₃ and G is CO₂—C₂H₅ (I-1'-5).

6. The method according to claim 1 wherein the ratio of the crop plant compatibility-improving compound to the compound of the formula (I-1') is from 0.001:1 to 1000:1.

7. The method according to claim 6 wherein the ratio is from 0.01:1 to 100:1.

8. The method according to claim 7 wherein the ratio is from 0.05:1 to 10:1.

9. The method according to claim 8 wherein the ratio is from 0.07:1 to 1.5:1.

10. The method according to claim 1 wherein the crop plant compatibility-improving compound is cloquintocet-mexyl.

11. The method according to claim 1 wherein the crop plant compatibility-improving compound is isoxadifen-ethyl.

12. The method according to claim 1 wherein the crop plant compatibility-improving compound is mefenpyr-diethyl.

13. The method according to claim 1 wherein the crop plant compatibility-improving compound is dichlormid.

14. The method according to claim 1 wherein the crop plant compatibility-improving compound is furilazole.

15. The method according to claim 1 wherein the crop plant compatibility-improving compound is fenclorim.

16. The method according to claim 1 wherein the crop plant compatibility-improving compound is the compound

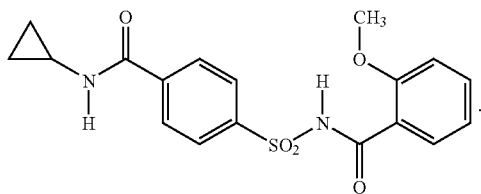

17. The method according to claim 1 wherein the composition consists essentially of a compound of formula (I-1') and a crop plant compatibility-improving compound.

18. The composition according to claim 2 wherein the ratio of the crop plant compatibility-improving compound to the compound of the formula (I-1') is from 0.001:1 to 1000:1.

19. The composition according to claim 18 wherein the ratio is from 0.01:1 to 100:1.

20. The composition according to claim 19 wherein the ratio is from 0.05:1 to 10:1.

21. The method according to claim 20 wherein the ratio is from 0.07:1 to 1.5:1.

22. The composition according to claim 2 wherein the crop plant compatibility-improving compound is cloquintocet-mexyl.

23. The composition according to claim 2 wherein the crop plant compatibility-improving compound is isoxadifen-ethyl.

24. The composition according to claim 2 wherein the crop plant compatibility-improving compound is mefenpyr-diethyl.

25. The composition according to claim 2 wherein the crop plant compatibility-improving compound is dichlormid.

26. The composition according to claim 2 wherein the crop plant compatibility-improving compound is furilazole.

27. The composition according to claim 2 wherein the crop plant compatibility-improving compound is fenclorim.

28. The composition according to claim 2 wherein the crop plant compatibility-improving compound is the compound

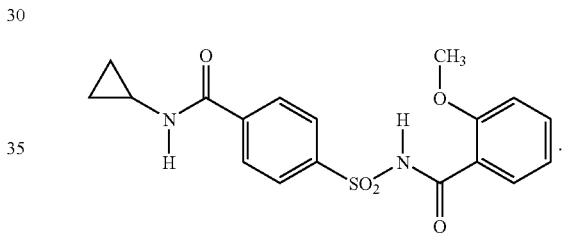

29. The composition according to claim 2 consisting essentially of the compound of formula (I-1') and the crop plant compatibility-improving compound.

* * * * *